US009459258B2

(12) United States Patent
Tang et al.

(10) Patent No.: US 9,459,258 B2
(45) Date of Patent: Oct. 4, 2016

(54) IDENTIFICATION AND QUANTIFICATION OF INTACT GLYCOPEPTIDES IN COMPLEX SAMPLES

(71) Applicants: INDIANA UNIVERSITY RESEARCH AND TECHNOLOGY CORPORATION, Indianapolis, IN (US); TEXAS TECH UNIVERSITY SYSTEM, Lubbock, TX (US)

(72) Inventors: Haixu Tang, Bloomington, IN (US); Yehia S. Mechref, Lubbock, TX (US)

(73) Assignees: INDIANA UNIVERSITY RESEARCH AND TECHNOLOGY CORP., Indianapolis, IN (US); TEXAS TECH UNIVERSITY SYSTEM, Lubbock, TX (US)

( * ) Notice: Subject to any disclaimer, the term of this patent is extended or adjusted under 35 U.S.C. 154(b) by 0 days.

(21) Appl. No.: 14/402,686

(22) PCT Filed: May 21, 2013

(86) PCT No.: PCT/US2013/041962
§ 371 (c)(1),
(2) Date: Nov. 21, 2014

(87) PCT Pub. No.: WO2013/177121
PCT Pub. Date: Nov. 28, 2013

(65) Prior Publication Data
US 2015/0160233 A1    Jun. 11, 2015

Related U.S. Application Data

(60) Provisional application No. 61/649,670, filed on May 21, 2012.

(51) Int. Cl.
| | | |
|---|---|---|
| G06G 7/58 | (2006.01) | |
| G01N 33/68 | (2006.01) | |
| C12Q 1/37 | (2006.01) | |
| G06F 19/00 | (2011.01) | |
| G01N 33/48 | (2006.01) | |

(52) U.S. Cl.
CPC ............ *G01N 33/6848* (2013.01); *C12Q 1/37* (2013.01); *G01N 33/6842* (2013.01); *G06F 19/70* (2013.01); *G01N 2440/38* (2013.01)

(58) Field of Classification Search
None
See application file for complete search history.

(56) References Cited

U.S. PATENT DOCUMENTS

| | | |
|---|---|---|
| 2006/0120961 A1 | 6/2006 | Schneider et al. |
| 2008/0118932 A1 | 5/2008 | Toler et al. |
| 2011/0136160 A1 | 6/2011 | Sanchez et al. |
| 2011/0295521 A1 | 12/2011 | Satulovsky et al. |
| 2012/0107858 A1 | 5/2012 | Yoo et al. |

OTHER PUBLICATIONS

ISA/US, International Search Report and Written Opinion for PCT/US2013/041962, Oct. 25, 2013, 14 pages.
Mayampurath et. al., DeconMSn: A software tool for accurate parent ion monoisotopic mass determination for tandem mass spectra. Bioinformatics. Apr. 1, 2008;24(7):1021-3.
Wu et. al. A Comp. Approach for the Identification of Site-Specific Protein Glycosylations Through Ion-Trap Mass Spectrometry, Lecture Notes in Comp Sci, 2007, 4532:96-107.
Steentoft, C., Vakhrushev, S.Y., Vester-Christensen, M.B., Schjoldager, K.T.B.G., Kong, Y., Bennett, E.P., Mandel, U., Wandall, H., Levery, S.B., and Clausen, H. (2011) Mining the O-glycoproteome using zinc-finger nuclease-glycoengineered SimpleCell lines. Nat Meth. 8(11),977-982.
Gerken, T.A., Jamison, O., Perrine, C.L., Collette, J.C., Moinova, H., Ravi, L., Markowitz, S.D., Shen, W., Patel, H., and Tabak, L.A. (2011) Emerging paradigms for the initiation of mucin type protein O-glycosylation by the polypeptide GalNAc transferase (ppGalNAc T) family of glycosyltransferases. Journal of Biological Chemistry.
Mechref, Y., Hu, Y., Garcia, A., Zhou, S., Desantos-Garcia, J.L., and Hussein, A. (2012) Defining putative glycan cancer biomarkers by MS. Bioanalysis. 4(20),2457-2469.
An, H.J., Kronewitter, S.R., Leoz, M.L.A.d., and Lebrilla, C.B. (2009) Glycomics and disease markers. Current Opinion in Chemical Biology. 13(5-6),601-607.
Lebrilla, C.B. and An, H.J. (2009) The prospects of glycan biomarkers for the diagnosis of diseases. Molecular BioSystems. 5(1),17-20.
Mechref, Y., Hu, Y., Garcia, A., and Hussein, A. (2012) Identifying cancer biomarkers by mass spectrometry-based glycomics. Electrophoresis. 33(12),1755-1767.
An, H.J., Miyamoto, S., Lancaster, K.S., Kirmiz, C., Li, B., Lam, K.S., Leiserowitz, G.S., and Lebrilla, C.B. (2006) Profiling of Glycans in Serum for the Discovery of Potential Biomarkers for Ovarian Cancer. Journal of Proteome Research. 5(7),1626-1635.
Kirmiz, C., Li, B., An, H.J., Clowers, B.H., Chew, H.K., Lam, K.S., Ferrige, A., Alecio, R., Borowsky, A.D., Sulaimon, S., Lebrilla, C.B., and Miyamoto, S. (2007) A Serum Glycomics Approach to Breast Cancer Biomarker. Molecullar and Cellular Proteomics. 6,43-55.
Zaia, J. (2010) Mass Spectrometry and Glycomics. OMICS: A Journal of Integrative Biology. 14(4),401-418.
Wuhrer, M., Catalina, I.M., Deelder, A.M., and Hokke, C.H. (2006) Glycoproteomics based on tandem mass spectrometry of glycopeptides. Journal of Chromatography B. 849(1),115-128.

(Continued)

*Primary Examiner* — Eric S DeJong
(74) *Attorney, Agent, or Firm* — Barnes & Thornburg LLP

(57) ABSTRACT

Illustrative embodiments of methods and apparatus for identifying one or more intact glycopeptides in a sample are disclosed. According to one illustrative embodiment, a method may comprise receiving data representing a plurality of mass spectra obtained from mass spectrometry of the sample, scoring data representing each of the plurality of mass spectra against data associated with target glycopeptides, and identifying one or more intact glycopeptides in the sample based at least in part on the scoring of the data representing each of the plurality of mass spectra.

21 Claims, 13 Drawing Sheets

(56) References Cited

OTHER PUBLICATIONS

Mechref, Y. (2001), Use of CID/ETD Mass Spectrometry to Analyze Glycopeptides, in Current Protocols in Protein Science, John Wiley & Sons, Inc.

Ethier, M., Saba, J.A., Spearman, M., Krokhin, O., Butler, M., Ens, W., Standing, K.G., and Perreault, H. (2003) Application of the StrOligo algorithm for the automated structure assignment of complex N-linked glycans from glycoproteins using tandem mass spectrometry. Rapid Communications in Mass Spectrometry. 17(24),2713-2720, 14 pages.

Lapadula, A.J., Hatcher, P.J., Hanneman, A.J., Ashline, D.J., Zhang, H., and Reinhold, V.N. (2005) Congruent Strategies for Carbohydrate Sequencing. 3. Oscar: An Algorithm for Assigning Oligosaccharide Topology from MSn Data. Analytical Chemistry. 77(19),6271-6279.

Goldberg, D., Bern, M., Parry, S., Sutton-Smith, M., Panico, M., Morris, H.R., and Dell, A. (2007) Automated N-Glycopeptide Identification Using a Combination of Single- and Tandem-MS. Journal of Proteome Research. 6 :(10),3995-4005.

Hongsachart, P., Huang-Liu, R., Sinchaikul, S., Pan, F.-M., Phutrakul, S., Chaung, Y.-M., and Chen, S.-T. (2009) Glycoproteomic analysis of WGA-bound glycoprotein biomarkers in sera from patients with lung adenocarcinoma. Electrophoresis. 30(7),1206-1220.

An, H.J., Tillinghast, J.S., Woodruff, D.L, Rocke, D.M., and Lebrilla, C.B. (2006) A New Computer Program (GlycoX) to Determine Simultaneously the Glycosylation Sites and Oligosaccharide Heterogeneity of Glycoproteins. Journal of Proteome Research. 5(10),2800-2808.

Wu, Y., Mechref, Y., Klouckova, I., Mayampurath, A.M., Novotny, M.V., and Tang, H. (2009) Mapping Site-specific Protein N-Glycosylations through Liquid Chromatography/Mass Spectrometry and Targeted Tandem Mass Spectrometry. Rapid Communications in Mass Spectrometry. 24(7),965-72.

Woodin, C.L., Hua, D., Maxon, M., Rebecchi, K.R., Go, EP., and Desaire, H. (2012) GlycoPep Grader: A Web-Based Utility for Assigning the Composition of N-Linked Glycopeptides. Analytical Chemistry. 84(11),4821-4829.

Segu, Z. and Mechref, Y. (2010) Characterizing protein glycosylation site through higher-energy C-trap dissociation. Rapid Communications in Mass Spectrometry. 24(9),1217-1225.

Catalina, I.M., Koeleman, C.A.M., Deelder, A.M., and Wuhrer, M. (2007) Electron transfer dissociation of N-glycopeptides: loss of the entire N-glycosylated asparagine side chain. Rapid Commun Mass Spectrom. 211053-1061.

Desaire, H. (Year) New Web-based Tools for Glycopeptide Analysis. in 4th Charles Warren Workshop. 2012. Athens, GA, USA.

Käll, L. and Vitek, O. (2011) Computational Mass Spectrometryâ€" Based Proteomics. PLoS Comput Biol. 7(12), e1002277, 7 pages.

Hill, E.G., Schwacke, J.H., Cornte-Walters, S., Slate, E.H., Oberg, A.L., Eckel-Passow, J.E., Therneau, T.M., and Schey, K.L. (2008) A Statistical Model for iTRAQ Data Analysis. Journal of Proteome Research. 7(8),3091-3101.

Oberg, A.L., Mahoney, D.W., Eckel-Passow, J.E., Malone, C.J., Wolfinger, R.D., Hill, E.G., Cooper, L.T., Onuma, O.K., Spiro, C., Therneau, T.M., and Bergen, I.I.I.H.R. (2008) Statistical Analysis of Relative Labeled Mass Spectrometry Data from Complex Samples Using ANOVA. Journal of Proteome Research. 7(1),225-233.

Karpievitch, Y., Stanley, J., Taverner, T., Huang, J., Adkins, J.N., Ansong, C., Heffron, F., Metz, T.O., Qian, W.-J., Yoon, H., Smith, R.D., and Dabney, A.R. (2009) A statistical framework for protein quantitation in bottom-up MS-based proteomics. Bioinformatics. 25(16),2028-2034.

Segu, Z.M., Hammad, L.A., and Mechref, Y. (2010) Rapid and efficient glycoprotein identification through microwave-assisted enzymatic digestion. Rapid communications in mass spectrometry. 24(23),3461-3468.

Perkins, D.N., Pappin, D.J.C., Creasy, D.M., and Cottrell, J.S. (1999) Probability-based protein identification by searching sequence databases using mass spectrometry data. Electrophoresis. 20(18),3551-3567.

Jain, E., Bairoch, A., Duvaud, S., Phan, I., Redaschi, N., Suzek, B.E., Martin, M.J., McGarvey, P., and Gasteiger, E. (2009) Infrastructure for the life sciences:design and implementation of the UniProt website. BMC Bioinformatics. 10 (136).

Consortium, T.U. (2011) Ongoing and future developments at the Universal Protein Resource. Nucl. Acids Res. 39214-219.

Jung, K., Cho, W., and Regnier, F.E. (2008) Glycoproteomics of Plasma Based on Narrow Selectivity Lectin Affinity Chromatography. Journal of Proteome Research. 8(2),643-650.

Madera, M., Mechref, Y., Klouckova, I., and Novotny, M.V. (2006) Semiautomated High-Sensitivity Profiling of Human Blood Serum Glycoproteins through Lectin Preconcentration and Multidimensional Chromatography/Tandem Mass Spectrometry. Journal of Proteome Research. 5(9),2348-2363.

Liu, T., Qian, W.-J., Gritsenko, M.A., Camp, D.G., Monroe, M.E., Moore, R.J., and Smith, R.D. (2005) Human Plasma N-Glycoproteome Analysis by Immunoaffinity Subtraction, Hydrazide Chemistry, and Mass Spectrometry. Journal of Proteome Research. 4(6),2070-2080.

Krambeck, F.J. and Betenbaugh, M.J. (2005) A Mathematical Model for N-linked Glycosylation. Biotech. & Bioengineering. 92(6),711-728.

Ranzinger, R. Herget, S., von der Lieth, C.-W., and Frank, M. (2011) GlycomeDB—a unified database for carbohydrate structures. Nucleic Acids Research. 39(suppl 1),D373-D376.

Horn, D.M., Zubarev, R.A., and McLafferty, F.W. (2000) Automated reduction and interpretation of high resolution electrospray mass spectra of large molecules. Journal of the American Society for Mass Spectrometry. 11(4),320-332.

Renard, B.Y., Kirchner, M., Monigatti, F., Ivanov, A.R., Rappsilber, J., Winter, D., Steen, J.A.J., Hamprecht, F.A., and Steen, H. (2009) When less can yield more—Computational preprocessing of MS/MS spectra for peptide identification. PROTEOMICS. 9(21),4978-4984.

Elias, J.E. and Gygi, S.P. (2007) Target-decoy search strategy for increased confidence in large-scale protein identifications by mass spectrometry. Nat Meth. 4(3),207-214.

Scott, N.E., Parker, B.L., Connolly, A.M., Paulech, J., Edwards, A.V.G., Crossett, B., Falconer, L., Kolarich, D., Djordjevic, S.P., HÄjrup, P., Packer, N.H., Larsen, M.R., and Cordwell, S.J. (2011) Simultaneous Glycan-Peptide Characterization Using Hydrophilic Interaction Chromatography and Parallel Fragmentation by CID, Higher Energy collisional Dissociation, and Electron Transfer Dissociation MS Applied to the N-Linked Glycoproteome of Campylobacter jejuni. Molecular & Cellular Proteomics. 10(2), 27 pages.

Mayampurath, A.M., Wu, Y., Segu, Z.M., Mechref, Y., and Tang, H. (2011) Improving confidence in detection and characterization of protein N-glycosylation sites and microheterogeneity. Rapid Communications in Mass Spectrometry. 25(14),2007-2019.

Käll, L., Storey, J.D., MacCoss, M.J., and Noble, W.S. (2007) Assigning Significance to Peptides Identified by Tandem Mass Spectrometry Using Decoy Databases. Journal of Proteome Research. 7(1),29-34.

Green, E.D., Adelt, G., Baenziger, J.U., Wilson, S., and Van Halbeek, H. (1988) The asparagine-linked oligosaccharides on bovine fetuin. Structural analysis of N-glycanasereleased oligosaccharides by 500-megahertz 1H NMR spectroscopy. Journal of Biological Chemistry. 263(34),18253-68.

Cooper, C.A., Joshi, H.J., Harrison, M.J., Wilkins, M.R., and Packer, N.H. (2003) GlycoSuiteDB: A curated relational database of glycoprotein glycan structures and their biological sources. 2003 update. Nucl. Acids Res. 31(1),511-513.

Raman, R., Venkatraman, M., Ramakrishnan, S., Lang, W., Raguram, S., and Sasisekharan, R. (2006) Advancing glycomics: Implementation stratergies at the Consortium for Functional Glycomics. Glycobiology. 16(5),82R-90R.

(56) References Cited

OTHER PUBLICATIONS

Aldredge, D., An, H.J., Tang, N., Waddell, K., and Lebrilla, C.B. (2012) Annotation of a Serum N-Glycan Library for Rapid Identification of Structures. Journal of Proteome Research. 11(3),1958-1968.

Ye, B., Cramer, D.W., Skates, S.J., Gygi, S.P., Pratomo, V., Fu, L., Horick, N.K., Licklider, L.J., Schorge, J.O., Berkowitz, R.S., and Mok, S.C. (2003) Haptoglobin-Î± Subunit as Potential Serum Biomarker in Ovarian Cancer: Identification and Characterization Using Proteomic Profiling and Mass Spectrometry. Clinical Cancer Research. 9 (8),2904-2911.

Lin, Z., Simeone, D.M., Anderson, M.A., Brand, R.E., Xie, X., Shedden, K.A., Ruffin, M.T., and Lubman, D.M. (2011) Mass Spectrometric Assay for Analysis of Haptoglobin Fucosylation in Pancreatic Cancer. Journal of Proteome Research. 10(5),2602-2611.

de Leoz, M.L.A., Young, L.J.T., An, H.J., Kronewitter, S.R., Kim, J., Miyamoto, S., Borowsky, A.D., Chew, H.K., and Lebrilla, C.B. High-Mannose Glycans are Elevated during Breast Cancer Progression. Molecular & Cellular Proteomics. 10(1), 13 pages.

Rutkowski, M.J., Sughrue, M.E., Kane, A.J., Mills, S.A., and Parsa, A.T. (2010) Cancer and the Complement Cascade. Molecular Cancer Research. 8(11),1453-1465.

Debruyne, E.N., Vanderschaeghe, D., Van Vlierberghe, H., Vanhecke, A., Callewaert, N., and Delanghe, J.R. (2010) Diagnostic Value of the Hemopexin N-Glycan Profile in Hepatocellular Carcinoma Patients. Clinical Chemistry. 56 (5),823-831.

Zhang, H., Li, X.-j., Martin, D.B., and Aebersold, R. (2003) Identification and quantification of N-linked glycoproteins using hydrazide chemistry, stable isotope labeling and mass spectrometry. Nat Biotech. 21(6),660-666.

Mayampurath, A., Yu, C.-Y., Mechref, Y., and Tang, H. (2011) Bioinformatic Approaches in Glycomics and Glycoproteomics. Current Proteomics. 8(4),309-324.

Mayampurath et al., Improving Confidence for Identification of Protein Glycosylation Using a Combination of HCD/CID Dissociation and a Unified Scoring Scheme, 57th ASMS Conference on Mass Spectrometry and Allied Topics. 2009, 2 pages.

```xml
<?xml version ="1.0" encoding="utf-8" standalone="yes"?>
<GlycoMap>
    <GlycoRecord>
        <ID>2</ID>
        <Mass>3944.600182</Mass>
        <NET>0.334891012</NET>
        <Protein>sp|P12763|FETUA_BOVIN</Protein>
        <Peptide>LCPDCPLLAPLNDSR</Peptide>
        <PeptideMass>1739.83349609375</PeptideMass>
        <Site>N155</Site>
        <Glycan>HexNAc * 4 + Hex * 5 + DeHex * 0 + NeuAc * 2 + NeuGc * 0</Glycan>
        <GlycanMass>2222.78235898438</GlycanMass>
        <RepresentativeCIDLength>390</RepresentativeCIDLength>
        <RepresentativeCIDSpectra>Q86EOkQq+W5D 0zJ6RFf9Q0PaLlEHocEQ9wawEQC68dD4yUIRJZfP0PjnkJ...DgsRDemlUT4UBdEStOG
                                                                                                        </RepresentativeCIDSpectra>

<RepresentativeHCDLength>501</RepresentativeHCDLength>
        <RepresentativeHCDSpectra>QsgArgAAAABCyAERAAAAAELIAXQAAAAAQta/4Q....04AAAAAQ/xiBwAAAABD/GMgAAAAAEP8ZDkAAAAA
                                                                                                        </RepresentativeHCDSpectra>

<RepresentativeETDLength>0</RepresentativeETDLength>
        <RepresentativeETDSpectra />
        <RepCIDScore>7</RepCIDScore>
        <RepHCDScore>2.6555990397587E-31</RepHCDScore>
        <RepETDScore>0</RepETDScore>
        <DatasetInfo>
            <DatasetRecord>
                <DatasetID>0</DatasetID>
                <DatasetName>Fetuin25MS900-090808-03.RAW</DatasetName>
                <DatasetType>Control</DatasetType>
                <Abundance>19810440</Abundance>
                <PrecursorMz>987.410515267195</PrecursorMz>

</DatasetRecord>

</DatasetRecord>
                <DatasetID>2</DatasetID>
                <DatasetName>Fetuin_101011_etd.raw<DatasetName>
                <DatasetType>Control</DatasetType>
                <Abundance>3710203</Abundance>
                <PrecursorMz>1316.54612667207<PrecursorMz>
                <PrecursorMass>3944.61262410206</PrecursorMass>

</DatasetRecord>
        </DatasetInfo>
    </GlycoRecord>
```

FIG. 7

IDENTIFICATION AND QUANTIFICATION OF INTACT GLYCOPEPTIDES IN COMPLEX SAMPLES

CROSS REFERENCE TO RELATED APPLICATIONS

This application is a national stage entry under 35 U.S.C. §371(b) of International Application Serial No. PCT/US2013/041962, filed May 21, 2013, which claims the benefit of U.S. Provisional Application No. 61/649,670, filed May 21, 2012, the entire disclosures of which are expressly incorporated by reference in their entirety.

STATEMENT REGARDING FEDERALLY SPONSORED RESEARCH

This invention was made with government support under DBI0642897 both awarded by the National Science Foundation and GM093322 awarded by the National Institutes of Health. The Government has certain rights in the invention.

TECHNICAL FIELD

The present disclosure relates, generally, to computational glycoproteomics and, more particularly, to the identification and quantification of intact glycopeptides in complex samples.

BACKGROUND ART

Glycans are chains of sugar residues that have a variety of biological functional attributes within cells from providing structural content to the modification of physical and chemical properties of proteins. Glycans are also involved in extrinsic roles such as intercellular communication and immune response to pathogen infections. As a common protein post-translational modification, glycosylation occurs where a glycan is linked to specific amino acid residues in a protein. N-Linked glycosylation (or N-glycosylation) involves the attachment of a sugar chain to any Asn in the motif Asn-Xaa-Ser/Thr (where Xaa can be any amino acid except proline). The attachment occurs prior to protein folding, implying that N-glycosylation affects the tertiary structure and stability of a glycoprotein. Another distinguishing characteristic of N-glycosylation is that all N-linked glycans (or N-glycans) share a common "pentamer" core structure consisting of two N-acteylglucosamine residues (GlcNAc) and three mannose (Man) residues. O-linked glycosylation (or O-glycosylation) involves the attachment of a glycan to a Ser/Thr residue and occurs mostly after protein folding. As a result, O-glycosylation is determined not only by the local peptide sequence, but also by the global tertiary structure of proteins, and there is no known sequence motif associated with O-glycosylation sites.

Glycans exhibit enormous structural diversity through the presence of branching structures, stereomeric configurations, and flexible glycosidic bonds, with O-linked glycans (or O-glycans) showing higher structural diversity than N-glycans. In addition, a majority of human proteins have been reported to be glycosylated, making glycosylation the most prevalent and heterogeneous post-translational modifications in human proteins. Given their role in physiological and pathological responses, many glycosylation events have been connected to human diseases. Glycan recognition is fundamental to host-microbe interaction, of which the infection of influenza viruses is the most studied. Glycosylation has also been associated with various cancers where variations in glycan and glycoprotein abundance have been observed in cancer patients in comparison with healthy individuals. This association warrants the study of glycosylation to develop potential disease biomarkers, especially from human serum samples. Although computational methods based on mass spectrometry data have proven to be effective in monitoring changes in the glycome, developing such methods for the glycoproteome could be challenging, largely due to the inherent complexity in simultaneously studying glycan structures and corresponding glycosylation sites.

DISCLOSURE OF INVENTION

The present invention may comprise one or more of the features recited in the appended claims and/or one or more of the following features and any combinations thereof.

A method of identifying one or more intact glycopeptides in a sample may comprise receiving data representing a plurality of mass spectra obtained from mass spectrometry of the sample, scoring data representing each of the plurality of mass spectra against data associated with target glycopeptides, and identifying one or more intact glycopeptides in the sample based at least in part on the scoring of the data representing each of the plurality of mass spectra.

Each of the one or more intact glycopeptides may comprise one or more glycans attached to a peptide. Identifying one or more intact glycopeptides in the sample may comprise identifying, for each of the one or more intact glycopeptides, one or more glycosylation sites at which the one or more glycans are attached to the peptide.

The one or more intact glycopeptides may comprise an N-linked glycopeptide. The one or more intact glycopeptides may comprise an O-linked glycopeptide. The sample may be a complex sample comprising a plurality of intact glycopeptides.

Receiving data representing a plurality of mass spectra may comprise receiving collision-induced dissociation (CID) data representing a plurality of mass spectra obtained after CID fragmentation, receiving high-energy C-trap dissociation (HCD) data representing a plurality of mass spectra obtained after HCD fragmentation, and receiving electron transfer dissociation (ETD) data representing a plurality of mass spectra obtained after ETD fragmentation.

Scoring data representing each of the plurality of mass spectra may comprise scoring HCD data associated with an ion from the sample and determining whether the ion from the sample is a glycopeptide ion based at least in part of the scoring of the HCD data.

Scoring data representing each of the plurality of mass spectra may further comprise scoring ETD data associated with a glycopeptide ion and identifying a candidate glycopeptide for the glycopeptide ion based at least in part on the scoring of the ETD data.

Scoring ETD data associated with the glycopeptide ion may comprise calculating a plurality of ETD scores by comparing the ETD data associated with the glycopeptide ion to a plurality of theoretical fragmentation spectra associated with a plurality of candidate glycopeptides.

Identifying one or more intact glycopeptides in the sample may comprise constructing a glycan sequence for the glycopeptide ion based at least in part on the candidate glycopeptide identified for the glycopeptide ion and the CID data associated with the glycopeptide ion.

The method of identifying one or more intact glycopeptides in a sample may further comprise scoring data representing each of the plurality of mass spectra against data associated with decoy glycopeptides and estimating a false detection rate (FDR) based at least in part on the scoring of the data representing each of the plurality of mass spectra against the data associated with target glycopeptides and the scoring of the data representing each of the plurality of mass spectra against the data associated with decoy glycopeptides. The FDR may comprise a ratio of a number of decoy ETD scores that exceed a threshold to a total number of ETD scores that exceed the threshold.

The method of identifying one or more intact glycopeptides in a sample may further comprise quantifying an abundance of one or more intact glycopeptides identified in the sample. Quantifying the abundance of one or more intact glycopeptides may comprise determining a spectral count of the one or more intact glycopeptides identified in the sample. The abundance of one or more intact glycopeptides in the sample may be increased in a sample associated with cancer as compared to a control sample.

The method of identifying one or more intact glycopeptides in a sample may further comprise performing tandem mass spectrometry on the sample to generate the data representing the plurality of mass spectra. Performing tandem mass spectrometry on the sample may comprise performing a mass spectrometry scan of the sample after collision-induced dissociation (CID) fragmentation, performing a mass spectrometry scan of the sample after high-energy C-trap dissociation (HCD) fragmentation, and performing a mass spectrometry scan of the sample after electron transfer dissociation (ETD) fragmentation.

One or more computer-readable media may comprise a plurality of instructions that, in response to being executed by one or more processors, result in the one or more processors performing any of the methods disclosed herein.

Apparatus may comprise at least one mass spectrometer, one or more processors, and one or more computer-readable media comprising a plurality of instructions that, in response to being executed by the one or more processors, result in the one or more processors performing any of the methods disclosed herein, wherein the one or more processors receive the data representing the plurality of mass spectra from the at least one mass spectrometer. At least one of the one or more processors may be configured to control operation of the at least one mass spectrometer to generate the data representing the plurality of mass spectra.

BRIEF DESCRIPTION OF DRAWINGS

The detailed description particularly refers to the accompanying figures in which:

FIG. 7 illustrates one embodiment of a glycomap in XML format;

BEST MODE(S) FOR CARRYING OUT THE INVENTION

Figure 1A:
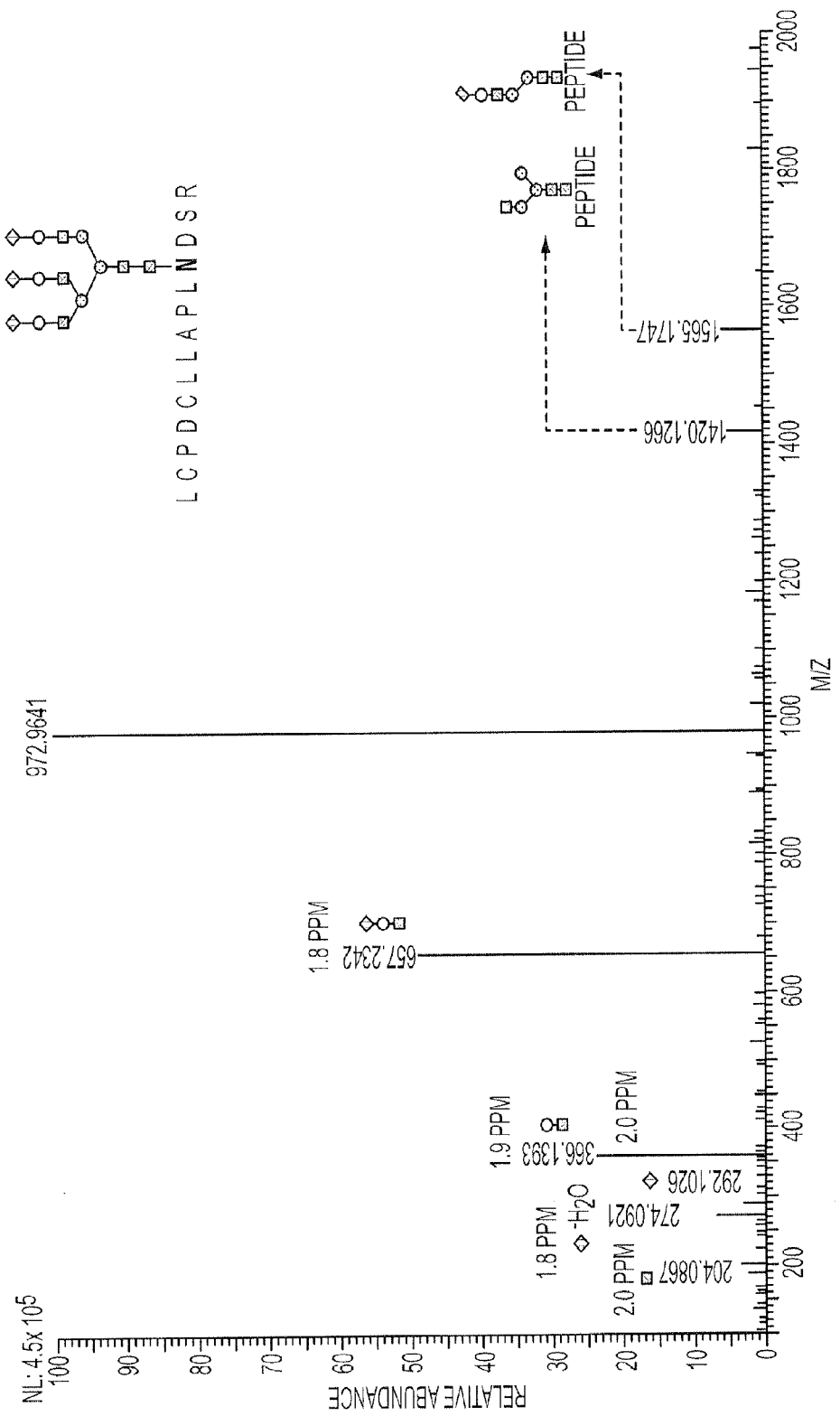
FIG. 1A illustrates one example of a high-energy C-trap dissociation (HCD) spectrum of a glycopeptide from Fetuin protein.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and appended claims.

In the following description, numerous specific details may be set forth in order to provide a more thorough understanding of the present disclosure. It will be appreciated, however, by one skilled in the art that embodiments of the invention may be practiced without such specific details. Full software instruction sequences have not been shown in detail in order not to obscure the invention. Those of ordinary skill in the art, with the included descriptions, will be able to implement appropriate functionality without undue experimentation.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Some embodiments of the invention may be implemented in hardware, firmware, software, or any combination thereof. By way of example, embodiments of the invention may be implemented as instructions carried by or stored on one or more machine-readable media, which may be read and executed by one or more processors. A machine-readable medium may be embodied as any device, mechanism, or physical structure for storing or transmitting information in a form readable by a machine (e.g., a computing device). For example, a machine-readable medium may be embodied as read only memory (ROM); random access memory (RAM); magnetic disk storage media; optical storage media; flash memory devices; mini- or micro-SD cards, memory sticks, electrical signals, and others.

The present disclosure introduces a computational framework for identifying intact N-linked glycopeptides (i.e., glycopeptides with N-linked glycans attached to glycosylation sites) in complex proteome samples. Within glycobiology, the use of mass spectrometry (MS) has been gaining popularity as means of analyzing both glycans and glycoproteins. Traditionally, glycans and their peptides have been studied as individual units using MS. According to the present disclosure, glycans and their peptides may beneficially be considered as a single unit, providing a holistic picture of glycosylation. Using multiple fragmentation techniques, such as collision-induced dissociation (CID), high-energy C-trap dissociation (HCD), and electron transfer dissociation (ETD), on enzymatically (e.g., trypsin) digested glycopeptides, information on both glycosylation site and glycan structure can be gleaned at the same time. Scoring algorithms are presented for tandem mass spectra of glycopeptides resulting from CID, HCD, and ETD fragmentation methods. The present disclosure focuses primarily on tryptically digested N-linked glycosylations and, unless noted otherwise, all references below to glycans and glycopeptides are of N-linked type.

Figure 1B:
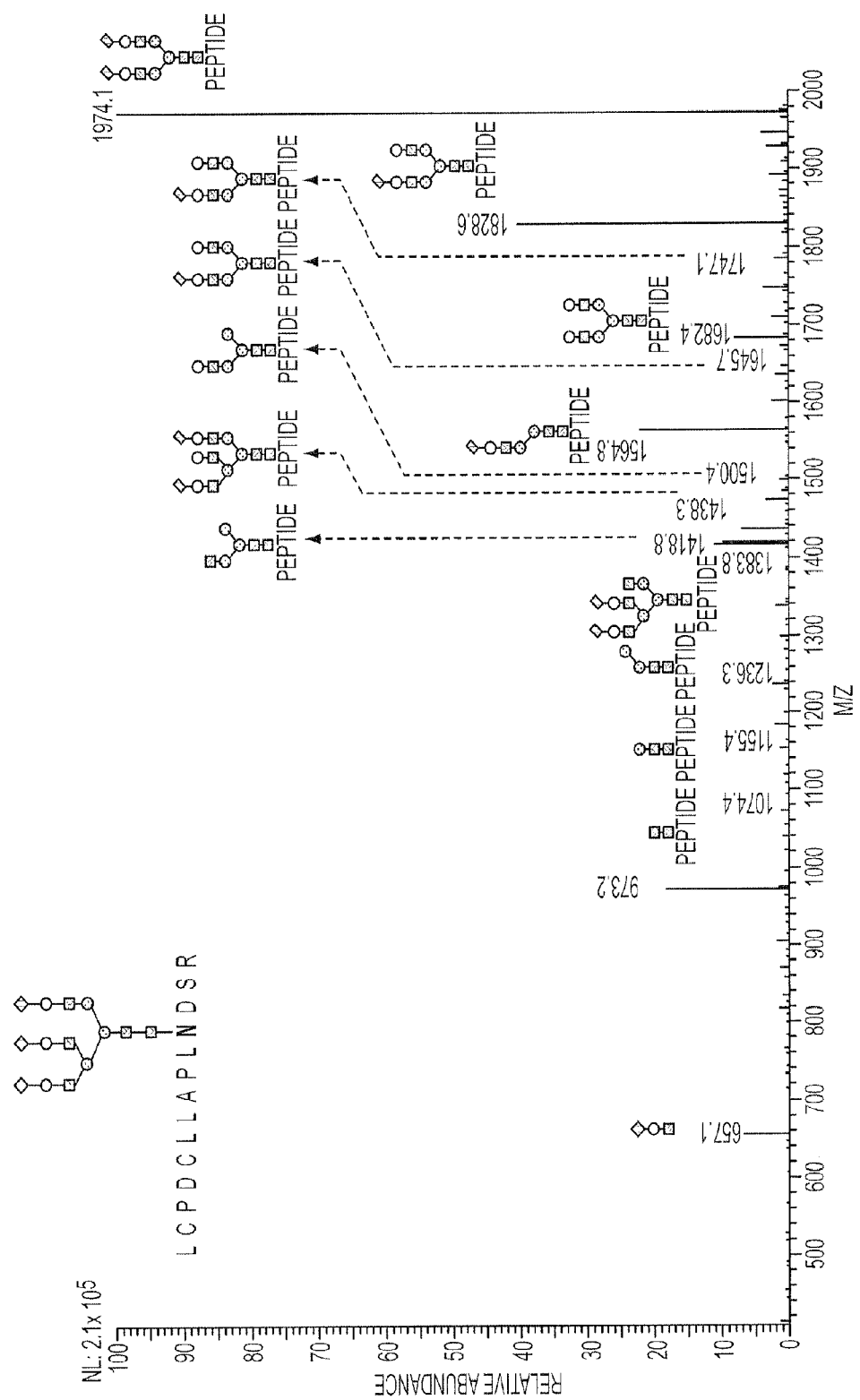
FIG. 1B illustrates one example of a collision-induced dissociation (CID) spectrum of a glycopeptide from Fetuin protein.
Figure 2A:
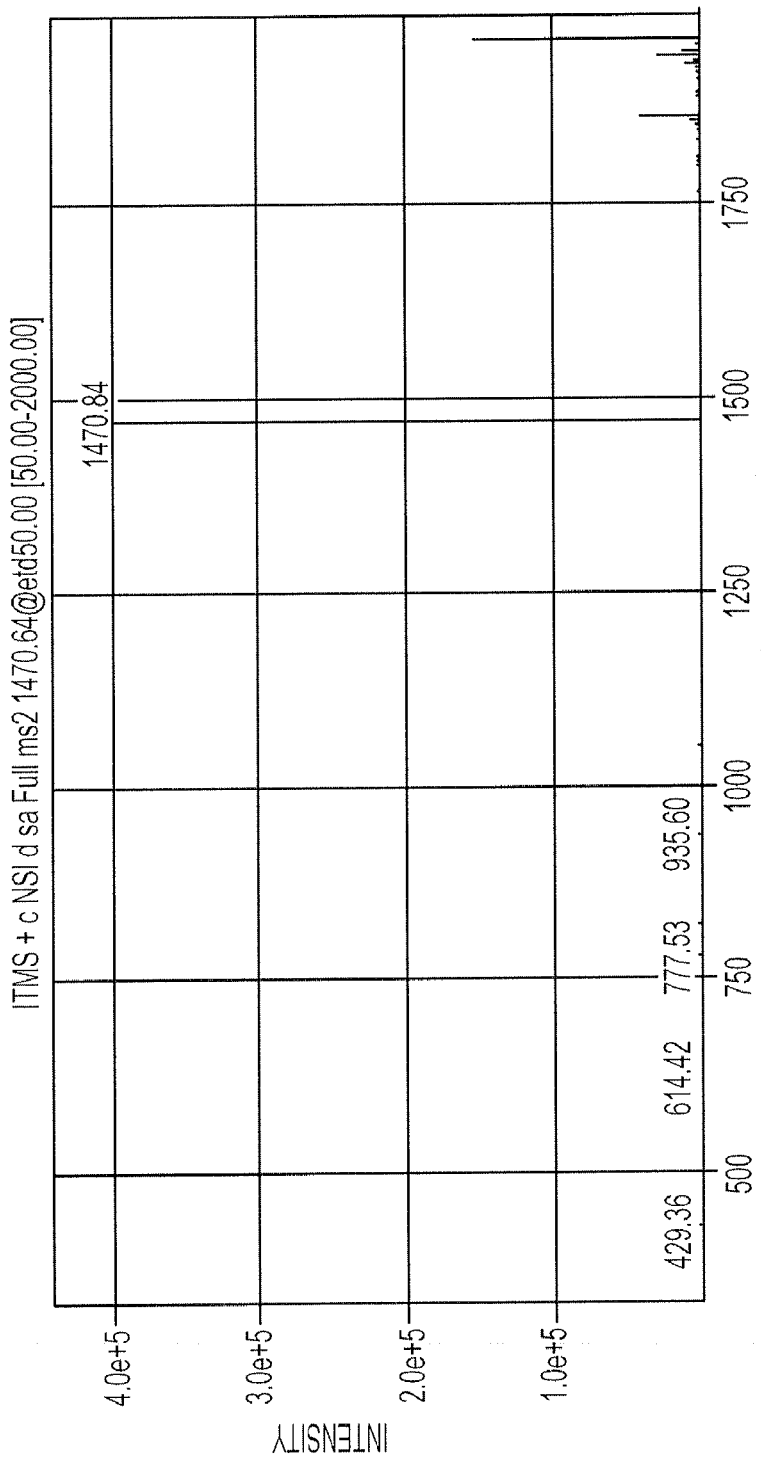
FIG. 2A illustrates one example of an electron transfer dissociation (ETD) spectrum of a glycopeptide from Fetuin protein.
Figure 2B:
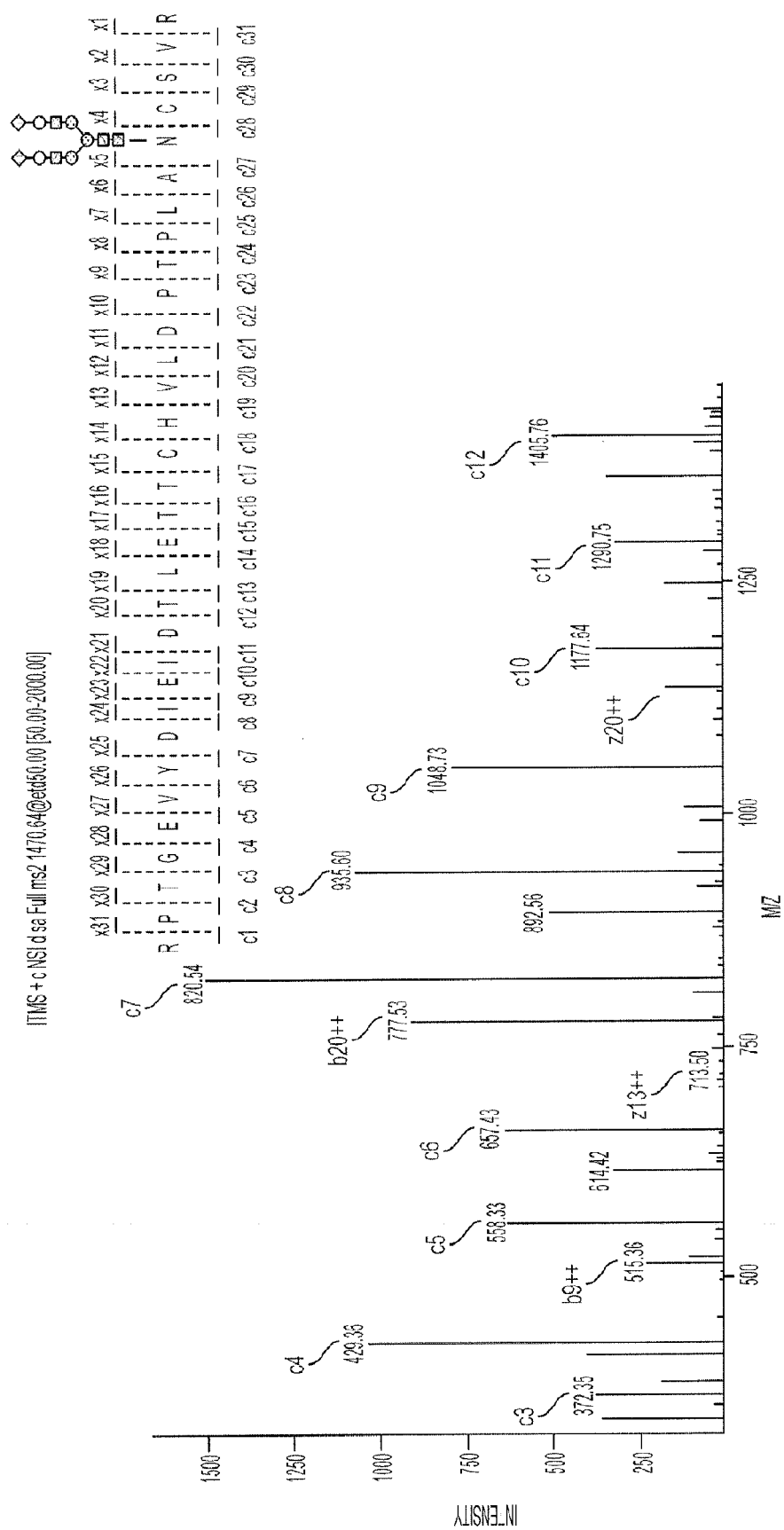
FIG. 2B illustrates a region of the ETD spectrum of FIG. 2A between 0 and parent m/z (1470.64)

In CID, the kinetic energy that accelerates the ions is converted to internal energy that breaks the linkage between molecules when the sample is collided with gas-phase neutral molecules. CID of N-glycopeptides using ion-trap MS/MS (IT-MS/MS) is dominated by B and Y ions that correspond to glycosidic fragmentation of the sugar chain. There may also be B and Y ions from the peptide fragmentation methods, but these are usually of minimal abundance because glycosidic bonds are weaker than peptide bonds and thus fragment easier. Previously developed bioinformatic tools have utilized CID fragmentation information along with precursor ion mass to reduce spurious hits. In HCD, which is typically coupled to CID, ions from monosaccharide, disaccharide or even trisaccharide can be observed with high mass accuracy that can be used to detect glycopeptides. ETD of glycopeptides involves the fragmentation of the peptide backbone producing primarily c and z product ions with intact glycan still mostly attached to the residue (although exceptions may be observed). While the HCD and CID spectra typically show intense fragment ions, as illustrated in FIGS. 1A and 1B, respectively, the informative fragments in ETD are typically of low abundance and present in the 0-parent m/z range. FIG. 2A illustrates ETD fragmentation of an example glycopeptide from fetuin sample, while FIG. 2B is zoomed in to illustrate the region between 0 and parent m/z (1470.64). Peaks corresponding to c and z fragmentation can be observed although at very low intensities.

The present disclosure introduces an informatics framework to characterize the intact glycopeptides in complex proteome samples, using novel scoring schemes of ETD spectra (to determine the peptide sequence) and a glycan sequencing algorithm from CID spectra (to characterize the glycan). The term "glycan sequence" is used to indicate a representation of glycans that contains monosaccharide composition and topology. The term "glycan sequencing" is used to denote an algorithm of constructing the topological arrangement of monosaccharides from CID spectra. The power of the presently disclosed methods may be further enhanced when multiple datasets are pooled together from replicates. Using the presently disclosed framework, 103 highly confident N-linked glycopeptides from 54 sites across 34 glycoproteins were identified from complex human serum proteome samples using conventional proteomic platforms without any glycopeptide enrichment.

The present disclosure also implements a target-decoy search approach in order to estimate a false discovery rate (FDR), so as to integrate these complementary scores for accurate glycopeptide assignments. The performance of the framework was demonstrated using simple mixtures of model glycoproteins, standard glycoprotein mixtures, and complex human serum samples. Notably, these samples were analyzed using liquid chromatography MS/MS (LC-MS/MS) protocols commonly used in proteomics without further enrichment of glycoproteins and glycopeptides. The present disclosure shows that a significant number of N-linked glycopeptides can be identified in complex human serum samples at high confidence level, demonstrating the applicability of this framework in studying complex glycoproteomes. In one illustrative embodiment, this framework may be implemented in a software tool that analyzes multiple pre-aligned LC-MS/MS datasets and reports a list (referred to herein as a "glycomap") of identified intact glycopeptides with their mass, elution time, and abundance.

The present disclosure also describes a novel statistical method for assessing quantitative alteration of protein glycosylation at site-specific levels. Currently, simple methods that measure the total glycoprotein expression do exist, but there are no algorithms that consider the source of the differences. In the present disclosure, a linear model based approach is developed that characterizes variations in glycoprotein abundance in a mass spectrometry-based quantification experiment. This model was applied to an esophageal cancer study based on blood serum samples to detect several potential N-linked glyco-biomarkers that show significant abundance alteration at glycopeptide level, but not at the corresponding glycoprotein level, indicating that the presently disclosed method is ready to be used for the discovery of biomarkers on site-specific glycosylations.

I. Experimental Procedures

In the illustrative embodiment, the following experimental procedures were used. It will be appreciated by those of skill in the art that, in other embodiments, additional or different experimental procedures may be used.

A. Materials

Bovine fetuin, human a1-acid glycoprotein (AGP), bovine pancreatic ribonuclease (RNase B), porcine thyroglobulin (PTG), and human fibronectin were purchased from Sigma-Aldrich (St. Louis, Mo.). DL-dithiothreitol (DTT), iodoacetamide (IAA), ammonium bicarbonate, and MS-grade formic acid were also obtained from Sigma-Aldrich (St. Louis, Mo.). HPLC-grade isopropanol and acetonitrile were acquired from Fisher Scientific (Pittsburgh, Pa.), while HPLC grade water was acquired from Mallinckrodt (Hazelwood, Mo.). Trypsin gold (mass spectrometry grade) was purchased from Promega (Madison, Wis.).

B. Depletion of the 7-Most Abundant Blood Serum Proteins

Agilent Plasma 7 multiple affinity removal spin (MARS) cartridge (Agilent Technologies, Santa Clara, Calif.) was used to deplete the 7-most abundant proteins, namely albumin, antitrypsin, IgA, IgG, transferin, haptoglobin, and fibrinogen. Two sets of blood serum samples were obtained from patients diagnosed with esophageal adenocarcinoma (cancer, N=15) and disease-free subjects (control, N=15). Two 15-μl aliquots of pooled human blood serum were depleted. The buffer of the depleted samples was exchanged into 50 mM ammonium bicarbonate using 5 kDa MWCO spin concentrators (Agilent Technologies, Santa Clara, Calif.).

C. Protein Assay

Prior to tryptic digestion, the protein concentrations of depleted cancer and control samples were determined by micro BCA protein assay (Thermo Scientific/Pierce, Rockford, Ill.). A bovine serum albumin (BSA) standard stock solution of 2.0 mg/ml concentration provided in the micro BCA assay kit was used to prepare a calibration curve spanning from 200 m/ml to 1 µg/ml. Ammonium bicarbonate (50 mM) buffer was used to prepare the BSA standard samples. The micro BCA working reagent required for the assay was prepared by mixing reagents A, B, and C (provided by the vendor) at a ratio of 50:48:3. Next, two 10-µl aliquots of samples were diluted in 140 µl of 50 mM ammonium bicarbonate buffer. BSA standard and the samples were then mixed with 150-µl aliquots of the working reagent and transferred to a 96-Well Plate prior to incubation at 37° C. for 2 hours. The concentration was then measured at 620 nm wavelength on Multiskan plate-reader (Thermo Scientific, Rockford, Ill.).

D. Tryptic Digestion of Model Glycoproteins

The 5 model glycoproteins (fetuin, AGP, RNase B, PTG, and fibronectin) were reduced by adding a 10-µl aliquot of 10 mM DTT prior to incubation at 60° C. for 45 min. The reduced model glycoproteins were then alkylated with the addition of a 20-µl aliquot of 20 mM IAA and incubation at 37.5° C. for 30 min in the dark. Unreacted IAA was consumed by the addition of a second 10-µl aliquot of 10 mM DTT. The reaction was allowed to proceed at 37.5° C. for 30 min in the dark. The samples were then tryptically digested at 37.5° C. overnight followed by microwave digestion at 45° C. and 50 W for 30 min. Tryptic digestion was quenched by the addition of a 0.5-µl aliquot of neat formic acid to the samples. Subsequently, these five standard glycoproteins (5SG) were mixed in the ratio of 2:2:4:1:1 w/w (fetuin:AGP:RNase B:PTG:fibronectin). Fetuin glycopeptides were also prepared for separate experiments.

E. Tryptic Digestion of Blood Serum Proteins

The depleted cancer and control proteins were thermally denatured at 65° C. for 10 min. A 1.25-µl aliquot of 200 mM DTT solution was added to the samples prior to incubation at 60° C. for 45 min. The samples were then alkylated by the addition of a 5-µl aliquot of 200 mM of IAA and incubation at 37.5° C. for 45 min in the dark. Excess IAA was consumed by adding a second aliquot of DTT and incubation at 37.5° C. for 30 min. This was followed by tryptic digestion involving the addition of trypsin and overnight incubation at 37.5° C. The amount of trypsin added to the samples (enzyme/substrate ratio of 1:25 w/w) was determined based on the protein concentration calculated from the BCA protein assay. To ensure complete enzymatic digestion, samples were subjected to microwave digestion at 45° C. and 50 W for 30 min. Finally, the enzymatic digestion was terminated by the addition of a 1-µl aliquot of neat formic acid.

F. LC-MS/MS Conditions

LC-MS/MS analysis was performed using Dionex 3000 Ultimate nano-LC system from Dionex (Sunnyvale, Calif.) interfaced to LTQ Orbitrap Velos mass spectrometer (Thermo Scientific, San Jose, Calif.) equipped with a nano-ESI source. The samples were online-purified using a PepMap 100 C18 cartridge (3 µm, 100 Å, Dionex) and separated using a PepMap 100 C18 capillary column (75 µm id×150 mm, 2 µm, 100 Å, Dionex). Solvent A was a 2% can aqueous solution containing 0.1% formic acid while solvent B was 98% ACN aqueous solution containing 0.1% formic acid. Tryptically digested fetuin, 5SG, and serum glycopeptides were analyzed with different liquid chromatography (LC) gradients and scan times. The first separation and scan time was set to 60 min. The separation of all fetuin and three datasets of 5SG was achieved using a reversed-phase gradient, 10% solvent B at 350 nl/min flow rate over 10 min, 10-45% over 35 min, 45-80% over 6 min, 80% over 4 min, 80-10% over 1 min, and 10% over 9 min. The second separation and scan time was set to 5 hours. One of 5SG datasets and all serum samples was separated based on 10% solvent B at 350 nl/min flow rate over 10 min, 10-35% over 260 min, 35-80% over 10 min, 80% over 18 min, 80-10% over 1 min, and 10% over 1 min.

An LTQ Orbitrap Velos mass spectrometer was operated with three scan events. The first scan event was a full MS scan (500-2000 m/z) with a mass resolution of 15,000. The second scan event was CID MS/MS of parent ions selected from the first scan event with an isolation width of 3.0 m/z, normalized collision energy (CE) of 35%, and an activation Q value of 0.250 with an activation time of 15 ms. The third scan event was HCD MS/MS of parent ions selected from the first scan event. The isolation width was 3.0 m/z while normalized CE was 45% with an activation time of 0.1 ms. The CID and HCD MS/MS were performed on the 8 most intense ions observed in the first scan event. Five technical replicates each for cancer and control serum were acquired using HCD/CID.

In a separate LC-MS/MS, ETD MS/MS was set up along with CID and HCD. The first scan event was a full MS scan and 15 scan events were followed alternating between CID, HCD, and ETD. This enabled MS/MS of the 5 most intense ions observed in the first scan. For ETD parameters, the isolation width was set to 4.0 m/z with the default charge state of 4. The reaction time was set to 100 ms and 150 ms allowing a supplemental activation. The LTQ Orbitrap Velos mass spectrometer was externally calibrated, permitting mass accuracy of less than 2 parts per million (ppm). One technical replicate each for cancer and control was acquired using CID, HCD and ETD.

G. Datasets and Databases

Three separate analysis were conducted: a simple glycoprotein (Fetuin) study, a mixture of standard glycoproteins (5SG) study and a complex serum (Serum) study. Details on the datasets and databases that were used in the present disclosure are summarized in Table 1 and Table 2 below. The Fetuin study involved three datasets, one of which had all three modes of fragmentation while the remaining two had only HCD/CID. All four datasets were HCD/CID/ETD in the 5SG study, which involved the analysis of samples containing five model glycoproteins: bovine fetuin, human a1-acid glycoprotein (AGP), bovine pancreatic ribonuclease (RNase B), porcine thyroglobulin (PTG), and human fibronectin, as described above. One of these 5SG datasets was run on a separate 5-hour column, as opposed to the rest which were run on a 2-hour column. The Serum study involved the pooling of serum samples into two groups (cancer and control) of six each, with one in each group being an HCD/CID/ETD dataset and the remaining five being HCD/CID.

TABLE 1

| Analysis Name | No. HCD/CID Datasets | No. HCD/ CID/ETD Datasets | Total Datasets | Comment(s) |
| --- | --- | --- | --- | --- |
| Fetuin | 2 | 1 | 3 | Fetuin sample on 1 hour LC |
| 5SG | 0 | 4 | 4 | Three datasets on 1 hour; one dataset on 5 hour LC |

TABLE 1-continued

| Analysis Name | No. HCD/CID Datasets | No. HCD/CID/ETD Datasets | Total Datasets | Comment(s) |
|---|---|---|---|---|
| Serum | 10 | 2 | 12 | Two sample types (cancer and control); all 5 hour LC |

Databases were built according to individual study type. The Fetuin study used a database constructed from a Fetuin A and B glycoproteins (referred to herein as "Fetuin_dB"). The 5SG study used a database constructed from a FASTA file containing the five model glycoproteins (referred to herein as "5SG_dB"). For the Serum study, the CID fragmentation spectra of each of the ten HCD/CID datasets were searched against the IPI database (version 3.79). Only identified proteins containing the glycosylation sequon were retained as putative glycoproteins. A list of 116 glycoproteins was obtained which was trimmed down to a list of 105 unique and reviewed UniProtKB/SwissProt IDs in the UniProtKB database (referred to herein as "SerumMascot_dB"). In order to test the robustness of all identifications, larger databases were also constructed. Both the Fetuin study and the 5SG study involved the analysis of the corresponding datasets against a database of 71 glycoproteins (referred to herein as "Test_dB"). Among these 71 glycoproteins, 2 were Fetuin, 5 were model glycoproteins from 5SG_dB, and the rest were randomly chosen from the SerumMascot_dB. In order to construct a larger database for the Serum study, the identified glycoproteins from previous serum glycoproteome studies were combined with glycoproteins in SerumMascot_dB. For each of these studies, the identified glycoproteins were mapped to unique and reviewed UniProtKB/Swissprot IDs in the UniProtKB database. In total, 566 glycoproteins were obtained from combining these four lists of glycoproteins and were compiled into a database (referred to herein as "SerumCombined_dB").

TABLE 2

| Database Name | No. Glycoproteins |
|---|---|
| Fetuin_dB | 2 |
| 5SG_dB | 5 |
| Test_dB | 71 |
| SerumMascot_dB | 105 |
| SerumCombined_dB | 566 |

The list putative glycans was created as follows. The glycans used in Mayampurath et al., "Improving Confidence for Identification of Protein Glycosylation Using a Combination of HCD/CID Dissociation and a Unified Scoring Scheme," 57th ASMS Conference on Mass Spectrometry and Allied Topics (2009), the entire disclosure of which is hereby incorporated by reference, were combined with glycans that were downloaded from GlycomeDB using a query based on presence of the common pentasaccharide core of N-linked glycans. Manual validation was performed to weed out glycan compositions that are not present in humans. These steps collectively resulted in a list of 319 glycan compositions that contained glycans of all three types (i.e., complex, hybrid, and highmannose) and also accounted for fucosylated and sialylated structures.

II. Computational Framework

A. Scoring CID/HCD Spectra of Glycopeptides

In the illustrative embodiment, the framework utilizes a scoring scheme for HCD that was introduced in Mayampurath et al., "Improving Confidence for Identification of Protein Glycosylation Using a Combination of HCD/CID Dissociation and a Unified Scoring Scheme," 57th ASMS Conference on Mass Spectrometry and Allied Topics (2009), the entire disclosure of which is hereby incorporated by reference. In that HCD scoring scheme, the presence of seven characteristic ions corresponding to mono-, di-, and trisaccharide combinations are tested in the HCD spectra. The p-value from this binomial distribution may be used in tandem with a length-of-longest-path-based CID scoring algorithm and accurate precursor deisotoping using the THRASH algorithm to facilitate confident detection of glycopeptide ions. Further, sialylated glycopeptides may be detected using the observance of N-acetylneuraminic acid (NeuAc) in HCD.

B. Scoring ETD Spectra of Glycopeptides

In order to score an ETD fragmentation spectrum, a set of target (i.e., candidate) glycopeptides is first constructed. For this purpose, a library of intact N-linked glycopeptides was built by attaching each N-glycan from the glycan list described above to peptides containing sequon(s) obtained from in-silico tryptic digest (allowing up to two mis-cleavages) of all glycoproteins in the target database (in FASTA format). Carbamidomethylation was considered as a fixed modification for each glycopeptide. For purposes of estimating FDR of glycopeptide identifications, a library of decoy glycopeptides is also constructed by attaching each of the above N-glycans to the reversed sequence of each tryptic peptide. The position of the sequon was kept intact while reversing the original peptide sequence, in order to construct a similar peptide sequence as the target glycopeptide sequence, thereby assuring better estimates of FDR. The target and decoy glycopeptides were combined to form a database against which the ETD fragmentation spectra may be searched. This was done for each of the databases listed in Table 2 above.

As illustrated in FIGS. 2A and 2B, ETD fragmentation of a glycopeptide typically results in low abundant fragments that are mostly observed at m/z values below that of the parent ion. The presently disclosed framework adopts a dual strategy for all peaks within a specified range. In a first pass, the top peak in a five Thompson (or m/z) bin is selected, thereby ensuring both resolution of peaks with isotopic signatures and the use a local noise threshold. Secondly, the top twenty overall observed peaks, excluding the precursor peak, are chosen for peak matching to theoretical fragments of glycopeptides. For each ETD spectrum, a list of target and decoy glycopeptides within 10 ppm of the precursor mass is considered from the database. For each candidate, a theoretical fragmentation spectrum is constructed using the peptide backbone with the attached glycan as an Asn (N) modification. Theoretical ion intensities are assigned as follows: c and z ions are considered with intensity of 100, b and y ions are considered with intensity of 50, and b and y ions neutral loss are considered with intensity of 25 each. These values were empirically assigned after manual validation of several annotated experimental spectra. While matching, both theoretical and observed spectra are binned into one Thompson bins. A bin is considered to be a "match" if both the corresponding theoretical and observed values are non-zero. Considering an observed spectrum of bin size n out of which m bins are found to be matched against a theoretical spectrum, the ETD score can be calculated as:

$$\text{ETD\_score} = \sum_{j=1}^{m} I_{j,theoretical} + \frac{\sum_{j=1}^{m} I_{j,observed}}{\sum_{i=1}^{n} I_{i,observed}}$$

Essentially, this ETD score is the summation of all matched theoretical intensities with a decimal component as the percentage of matched observed intensity. Glycopeptide candidates with two or more sequons are considered separately for each sequon position. The match with the highest ETD score is retained as the best match, with either a TRUE or FALSE designation depending on whether the highest scoring match corresponds to a target glycopeptide or a decoy glycopeptide, respectively.

C. Estimating FDR of Glycopeptide Identifications Based on ETD Scoring

After all ETD fragmentation spectra are scored for all glycopeptide candidates that were within a specified tolerance of parent monoisotopic mass, an ETD-based FDR may be estimated by sorting all spectra in decreasing order of their ETD score. For each scan, the FDR may then be allocated as the ratio of the number of decoy identifications with a higher ETD score to the total number of scans with a higher ETD score.

D. Glycan Sequencing Using CID Spectra

In the illustrative embodiment, the framework also implements a de novo sequencing algorithm using the CID spectrum in order to annotate the glycan component(s) of an N-linked glycopeptide. In the illustrative embodiment, this heuristic algorithm uses only the CID spectrum, the peptide mass-over-charge ratio (m/z) or the peptide sequence, the parent charge state, and the parent m/z as inputs. The algorithm starts from the position of the y1 ion, derived from the peptide mass plus one GlcNAc mass and incorporating an appropriate charge (which usually carries one less charge than the parent charge). Since all N-linked glycans have the same pentasaccharide core ($GluNAc_2Man_3$), the algorithm predicts the next m/z values continuously until the core is completed and accounted for in the spectrum. In the illustrative embodiment, the algorithm includes allowances for a fucosylated core GlcNAc thereby expanding the search pool of glycans.

The algorithm proceeds to grow the glycan outside the core in a non-linear fashion based upon the peaks observed in the CID spectrum. Peak matching is done with an empirically chosen tolerance of 0.8 m/z. In order to limit the size of the candidate search space at every step, the algorithm uses a set of glycan synthesis rules emulating the N-glycan synthesis process to guide the sequencing procedure. For example, fucose can only be attached to a GlcNAc and not a Man or a Gal. The complete set of rules used in the illustrative embodiment is set forth below in Table 3 and Table 4. In particular, Table 3 includes a list of enzymes and substrates involved in N-linked glycan synthesis. These reactions are used as a guide for growing the non-linear part of the N-glycan in order to select candidates to add to the search at each round of pool to spectrum matching. Combining these with the additional rules listed in Table 4 allows a reduction in size of the N-glycan sequence candidate pool.

Figure 3:
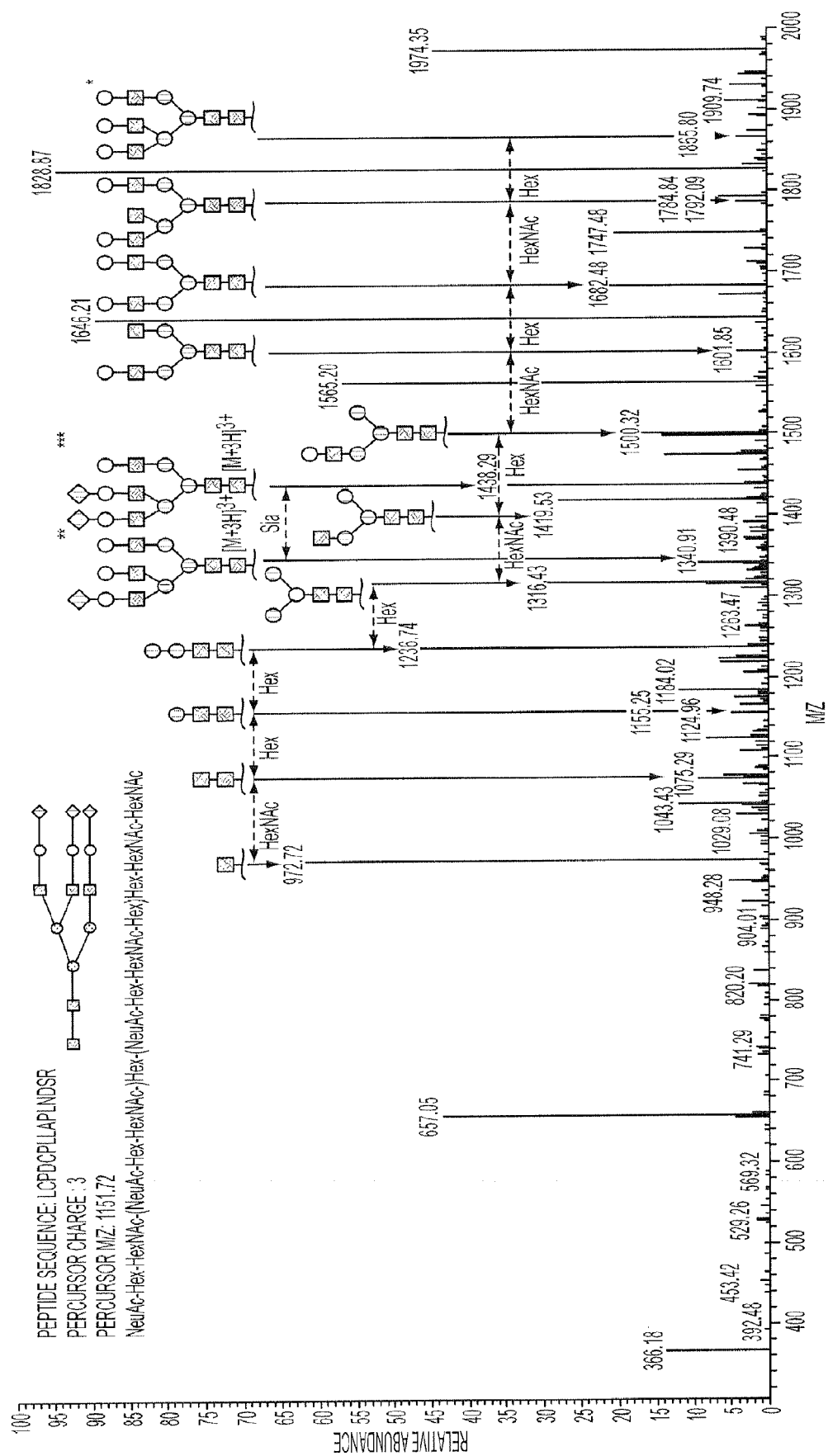
FIG. 3 illustrates one embodiment of the operation of a glycan sequencing algorithm.

Given a glycan sequence from the candidate pool, the algorithm will add each putative monosaccharide to this sequence, calculate the total glycan m/z, and match it to observed peaks in the CID spectrum. If there is a match, the new monosaccharide is attached to the partial glycan sequence based on the glycotransferase rules and the updated sequence is inserted into the candidate pool for the next round. This attaching and matching procedure begins with the core and continues until the maximum observed m/z is reached in the CID spectrum. One illustrative example of the algorithm's operation is illustrated in FIG. 3. Starting with the y1 ion at 972.72 m/z, the core was grown till completion at 1316.43 m/z. Next, each monosaccharide was continuously added and peak matched until the m/z limit reached beyond the observed m/z range in the CID spectrum (as illustrated by the glycan marked with the * at 1865.80 m/z). Usually, at this point, the parent m/z is utilized to select the monosaccharides that filled the missing segments. If successful, the algorithm is terminated, and the completed sequence or the closest glycopeptide candidate to the precursor mass within a user-defined tolerance (e.g., 80 ppm) is returned.

Many CID spectra, however, have one or more missing peaks that hamper the sequencing. While the algorithm has the functionality to add a di- and tri-saccharide to a partial glycan sequence (thereby accounting for up to 2 missing fragments), the algorithm may still sometimes return an incomplete sequence, primarily because of charge state difference. While the almost-complete glycan sequence carried a charge that was typically one less than the precursor, sometimes the fragment ions were observed to carry an extra charge. In order to account for this, the algorithm increases the charge state by 1 and repeats the sequencing procedure starting from the beginning of the CID spectrum. This iterative procedure is also illustrated in FIG. 3, in which the first pass of the glycan sequencing algorithm was done with charge state +2 and terminated at 1865.80 m/z (marked with * in FIG. 3). Upon incrementing the charge state to +3, the algorithm detects the matching candidate, marked with  (the peak at 1340.91 m/z) and * (the peak at 1438.29 m/z). The terminal NeuAc mono-saccharide was added based the m/z difference between the sequenced glycopeptide and the parent as mentioned above. The final output of the sequencing algorithm is the complete N-glycan sequence, or the top-ranked partial N-glycan sequence, encoded as an IUPAC string along with a matching score calculated as the log-2 of the summed matched intensities in the CID spectrum. While the illustrative embodiment of the glycan sequencing algorithm described above is used for N-linked glycans, it is contemplated that a different set of synthesis rules pertaining to O-linked glycans might be used to facilitate O-glycan sequencing.

TABLE 3

| Enzyme | Substrate |
| --- | --- |
| beta-galactoside alpha-2,6-sialyltransferase | CMP-N-acetylneuraminate + beta-D-galactosyl-1,4-N-acetyl-beta-D-glucosamine |
| monosialoganglioside sialyltransferase | CMP-N-acetylneuraminate + D-galactosyl-N-acetyl-D-galactosaminyl-(N-acetylneuraminyl)-D-galactosyl-D-glucosyl-(1<—>1)-ceramide |
| alpha-N-acetylgalactosaminide alpha-2,6-sialyltransferase | CMP-N-acetylneuraminate + glycano-1,3-(N-acetyl-alpha-D-galactosaminyl)-glycoprotein |
| | CMP-N-acetylneuraminate + protein MUC1-MFP6 |
| beta-galactoside alpha-2,3-sialyltransferase | CMP-N-acetylneuraminate + beta-D-galactosyl-1,3-N-acetyl-alpha-D-galactosaminyl-R |
| | CMP-N-acetylneuraminate + beta-D-galactosyl-O-R |

TABLE 3-continued

| Enzyme | Substrate |
|---|---|
| galactosyldiacylglycerol alpha-2,3-sialyltransferase | CMP-N-acetylneuraminate + 1,2-diacyl-3-beta-D-galactosyl-sn-glycerol<br>CMP-N-acetylneuraminate + Galbeta1-3GlcNAcbeta1-3Galbeta1-4Glc<br>CMP-N-acetylneuraminate + Galbeta1-3GlcNAcR<br>CMP-N-acetylneuraminate + Galbeta1-4GlcNAc<br>CMP-N-acetylneuraminic acid + 1,2-diacyl-3-beta-D-galactosyl-sn-glycerol<br>CMP-N-acetylneuraminic acid + NeuAcalpha-(2-3)-Galbeta-(1-4)-GlcNAcbeta-1-octyl |
| N-acetyllactosaminide alpha-2,3-sialyltransferase | CMP-N-acetylneuraminate + beta-D-galactosyl-(1->4)-N-acetyl-D-glucosaminyl-glycoprotein |
| alpha-N-acetylneuraminyl-2,3-beta-galactosyl-1,3-N-acetylgalactosaminide 6-alpha-sialyltransferase | CMP-N-acetylneuraminate + N-acetyl-alpha-neuraminyl-(2->3)-beta-D-galactosyl-(1->3)-N-acetyl-D-galactosaminyl-R |
| alpha-N-acetylneuraminate alpha-2,8-sialyltransferase | CMP-N-acetylneuraminate + alpha-N-acetylneuraminyl-(2->3)-beta-D-galactosyl-R |
| lactosylceramide alpha-2,3-sialyltransferase | CMP-N-acetylneuraminate + beta-D-galactosyl-(1->4)-beta-D-glucosyl-(1<—>1)-ceramide |
| neolactotetraosylceramide alpha-2,3-sialyltransferase | CMP-N-acetylneuraminate + beta-D-galactosyl-(1->4)-N-acetyl-beta-D-glucosaminyl-(1->3)-beta-D-galactosyl-(1->4)-D-glucosyl-(1<—>1)-ceramide |
| lactosylceramide alpha-2,6-N-sialyltransferase | CMP-N-acetylneuraminate + beta-D-galactosyl-(1->4)-beta-D-glucosyl-(1<—>1)-ceramide |
| 3-galactosyl-N-acetylglucosaminide 4-alpha-L-fucosyltransferase | GDP-beta-L-fucose + beta-D-galactosyl-(1->3)-N-acetyl-D-glucosaminyl-R |
| glycoprotein 6-alpha-L-fucosyltransferase | GDP-beta-L-fucose + N4-{N-acetyl-beta-D-glucosaminyl-(1->2)-alpha-D-mannosyl-(1->3)-[N-acetyl-beta-D-glucosaminyl-(1->2)-alpha-D-mannosyl-(1->6)]-beta-D-mannosyl-(1->4)-N-acetyl-beta-D-glucosaminyl-(1->4)-N-acetyl-beta-D-glucosaminyl}asparagine |
| galactoside 2-alpha-L-fucosyltransferase | GDP-beta-L-fucose + beta-D-galactosyl-(1->3)-N-acetyl-beta-D-glucosaminyl-(1->3)-beta-D-galactosyl-(1->4)-beta-D-glucosyl-(1<—>1)-ceramide |
| 4-galactosyl-N-acetylglucosaminide 3-alpha-L-fucosyltransferase | GDP-beta-L-fucose + (1->4)-beta-D-galactosyl-N-acetyl-D-glucosaminyl-R |
| glycoprotein 3-alpha-L-fucosyltransferase | GDP-beta-L-fucose + N4-{N-acetyl-beta-D-glucosaminyl-(1->2)-alpha-D-mannosyl-(1->3)-[N-acetyl-beta-D-glucosaminyl-(1->2)-alpha-D-mannosyl-(1->6)]-beta-D-mannosyl-(1->4)-N-acetyl-beta-D-glucosaminyl-(1->4)-N-acetyl-beta-D-glucosaminyl}asparagine |
| ursodeoxycholate N-acetylglucosaminyltransferase | UDP-N-acetyl-D-glucosamine + ursodeoxycholate |
| chitin synthase | UDP-GlcNAc + GlcNAc<br>6-O-dansyl-N-acetylglucosamine + [1,4-(N-acetyl-beta-D-glucosaminyl)]n<br>acetyl-D-glucosamine + [1,4-(N-acetyl-beta-D-glucosaminyl)]n<br>UDP-N-acetyl-D-glucosamine + N-acetyl-D-glucosamine<br>UDP-N-acetyl-D-glucosamine + [1,4-(N-acetyl-beta-D-glucosaminyl)]n |
| steroid N-acetylglucosaminyltransferase | UDP-N-acetyl-D-glucosamine + estradiol-17alpha 3-D-glucuronoside |
| lipopolysaccharide N-acetylglucosaminyltransferase | UDP-N-acetyl-D-glucosamine + lipopolysaccharide |
| poly(ribitol-phosphate) N-acetylglucosaminyltransferase | UDP-N-acetyl-D-glucosamine + poly(ribitol phosphate) |
| protein N-acetylglucosaminyltransferase | UDP-N-acetyl-D-glucosamine + [protein]-L-asparagine |
| alpha-1,3-mannosyl-glycoprotein 2-beta-N-acetylglucosaminyltransferase | UDP-N-acetyl-D-glucosamine + 3-(alpha-D-mannosyl)-beta-D-mannosyl-R |
| beta-1,3-galactosyl-O-glycosyl-glycoprotein beta-1,6-N-acetylglucosaminyltransferase | UDP-N-acetyl-D-glucosamine + beta-D-galactosyl-(1->3)-N-acetyl-D-galactosaminyl-R |
| mannotetraose 2-alpha-N-acetylglucosaminyltransferase | UDP-N-acetyl-D-glucosamine + (1->3)-alpha-D-mannosyl-(1->2)-alpha-D-mannosyl-(1->2)-alpha-D-mannosyl-D-mannose |
| N-acetylglucosaminyldiphosphodolichol N-acetylglucosaminyltransferase | UDP-N-acetyl-D-glucosamine + N-acetyl-D-glucosaminyl-diphosphodolichol |
| alpha-1,6-mannosyl-glycoprotein 2-beta-N-acetylglucosaminyltransferase | UDP-N-acetyl-D-glucosamine + 6-(alpha-D-mannosyl)-beta-D-mannosyl-R |
| beta-1,4-mannosyl-glycoprotein 4-beta-N-acetylglucosaminyltransferase | UDP-N-acetyl-D-glucosamine + beta-D-mannosyl-R |

TABLE 3-continued

| Enzyme | Substrate |
|---|---|
| alpha-1,3-mannosyl-glycoprotein 4-beta-N-acetylglucosaminyltransferase | UDP-N-acetyl-D-glucosamine + 3-(2-[N-acetyl-beta-D-glucosaminyl]-alpha-D-mannosyl)-beta-D-mannosyl-R |
| beta-1,3-galactosyl-O-glycosyl-glycoprotein beta-1,3-N-acetylglucosaminyltransferase | UDP-N-acetyl-D-glucosamine + beta-D-galactosyl-(1->3)-[N-acetyl-D-glucosaminyl-(1->6)]-N-acetyl-D-galactosaminyl-R |
| acetylgalactosaminyl-O-glycosyl-glycoprotein beta-1,3-N-acetylglucosaminyltransferase | UDP-N-acetyl-D-glucosamine + N-acetyl-beta-D-galactosaminyl-R |
| acetylgalactosaminyl-O-glycosyl-glycoprotein beta-1,6-N-acetylglucosaminyltransferase | UDP-N-acetyl-D-glucosamine + N-acetyl-beta-D-glucosaminyl-1,3-N-acetyl-D-galactosaminyl-R |
| N-acetyllactosaminide beta-1,3-N-acetylglucosaminyltransferase | UDP-N-acetyl-D-glucosamine + beta-D-galactosyl-(1->4)-N-acetyl-D-glucosaminyl-R |
| N-acetyllactosaminide beta-1,6-N-acetylglucosaminyl-transferase | UDP-N-acetyl-D-glucosamine + beta-D-galactosyl-(1->4)-N-acetyl-D-glucosaminyl-R |
| dolichyl-phosphate alpha-N-acetylglucosaminyltransferase | UDP-N-acetyl-D-glucosamine + dolichyl phosphate |
| alpha-1,6-mannosyl-glycoprotein 6-beta-N-acetylglucosaminyltransferase | UDP-N-acetyl-D-glucosamine + 6-(2-[N-acetyl-beta-D-glucosaminyl]-alpha-D-mannosyl)-beta-D-mannosyl-R |
| beta-galactosyl-N-acetylglucosaminylgalactosylglucosyl-ceramide beta-1,3-acetylglucosaminyltransferase | UDP-N-acetyl-D-glucosamine + beta-D-galactosyl-(1->4)-N-acetyl-beta-D-glucosaminyl-(1->3)-beta-D-galactosyl-(1->4)-beta-D-glucosyl-(1<—>1)-ceramide |
| galactosyl-N-acetylglucosaminylgalactosylglucosyl-ceramide beta-1,6-N-acetylglucosaminyltransferase | UDP-N-acetyl-D-glucosamine + D-galactosyl-(1->4)-N-acetyl-beta-D-glucosaminyl-(1->3)-beta-D-galactosyl-(1->4)-beta-D-glucosyl-(1<—>1 )-ceramide |
| high-mannose-oligosaccharide beta-1,4-N-acetylglucosaminyltransferase | UDP-N-acetyl-D-glucosamine + O-mannopyranosyl-alpha-1,3-[O-mannopyranosyl-alpha-1,3-(O-mannopyranosyl-alpha-1,6)-O-mannopyranosyl-alpha-1,6]-O-mannopyranosyl-beta-1,4-N-acetyl-D-glucosamine |
| phosphatidylinositol N-acetylglucosaminyltransferase | UDP-N-acetyl-D-glucosamine + 1-phosphatidyl-1D-myo-inositol |
| alpha-1,6-mannosyl-glycoprotein 4-beta-N-acetylglucosaminyltransferase | UDP-N-acetyl-D-glucosamine + 2,6-bis(N-acetyl-beta-D-glucosaminyl)-alpha-D-mannosyl-R |
| lactosylceramide 1,3-N-acetyl-beta-D-glucosaminyltransferase | UDP-N-acetyl-D-glucosamine + beta-D-galactosyl-(1->4)-beta-D-glucosyl-(1<—>1)-ceramide |
| O-fucosylpeptide 3-beta-N-acetylglucosaminyltransferase | UDP-beta-D-GlcNAc + PCQNGGS(O-beta-L-fucosyl)-CKDQL |
| glucuronyl-galactosyl-proteoglycan 4-alpha-N-acetylglucosaminyltransferase | UDP-N-acetyl-D-glucosamine + beta-D-glucuronosyl-(1->3)-beta-D-galactosyl-(1->3)-beta-D-galactosyl-(1->4)-beta-D-xylosyl-proteoglycan |
| glucuronosyl-N-acetylglucosaminyl-proteoglycan 4-alpha-N-acetylglucosaminyltransferase | UDP-N-acetyl-D-glucosamine + beta-D-glucuronosyl-(1->4)-N-acctyl-alpha-D-glucosaminyl-proteoglycan |
| undecaprenyldiphospho-muramoylpentapeptide beta-N-acetylglucosaminyltransferase | UDP-N-acetylglucosamine + Mur2Ac(oyl-L-Ala-gamma-D-Glu-L-Lys-D-Ala-D-Ala)-diphosphoundecaprenol |
| [Skp1-protein]-hydroxyproline N-acetylglucosaminyltransferase | UDP-N-acetylglucosamine + [Skp1-protein]-hydroxyproline |
| protein O-GlcNAc transferase | UDP-N-acetyl-D-glueosamine:protein-O-beta-N-acetyl-D-glucosaminyl transferase |
| UDP-N-acetylglucosamine 1-carboxyvinyltransferase | phosphoenolpyruvate + UDP-N-acetyl-D-glucosamine |
| loliose synthase | UDP-galactose + sucrose |
| lactose synthase | UDP-galactose + D-glucose |
| sphingosine beta-galactosyltransferase | UDPgalactose + D-1,3,4-trihydroxy-2-aminooctadecane |
| | UDPgalactose + DL-erythro-1,3-dihydroxy-2-amino-4-cis-octadecene |
| | UDPgalactose + DL-erythro-trans-sphingosine |
| | UDPgalactose + DL-threo-1,3-dihydroxy-2-amino-4-cis-octadecene |
| | UDPgalactose + DL-threo-1,3-dihydroxy-2-amino-4-octadecyne |
| | UDPgalactose + DL-threo-1,3-dihydroxy-2-amino-4-trans-heptadecene |
| | UDPgalactose + DL-threo-1,3-dihydroxy-2-amino-4-trans-nonadecene |
| | UDPgalactose + DL-threo-1,3-dihydroxy-2-amino-4-trans-octadecene |
| | UDPgalactose + DL-threo-1,3-dihydroxy-2-aminooctadecane |
| | UDPgalactose + N-acetyl-DL-threo-trans-sphingosine |

TABLE 3-continued

| Enzyme | Substrate |
|---|---|
| fucosylgalactoside 3-alpha-galactosyltransferase | UDP-galactose + alpha-L-fucosyl-(1->2)-D-galactosyl-R |
| beta-N-acetylglucosaminylglycopeptide beta-1,4-galactosyltransferase | UDP-galactose + N-acetyl-beta-D-glucosaminylglycopeptide |
| lipopolysaccharide 3-alpha-galactosyltransferase | UDP-galactose + lipopolysaccharide |
| 2-hydroxyacylsphingosine 1-beta-galactosyltransferase | UDP-galactose + 2-(2-hydroxyacyl)sphingosine |
| 2-hydroxyacylsphingosine 1-beta-galactosyltransferase | UDP-galactose + 2-(2-hydroxyacyl)sphingosine |
| N-acylsphingosine galactosyltransferase | UDP-galactose + N-acylsphingosine |
| procollagen galactosyltransferase | UDP-galactose + procollagen 5-hydroxy-L-lysine |
| ganglioside galactosyltransferase | UDP-galactose + N-acetyl-D-galactosaminyl-(N-acetylneuraminyl)-D-galactosyl-1,4-beta-D-glucosyl-N-acylsphingosine |
| galactinol-raffinose galactosyltransferase | alpha-D-galactosyl-(1->3)-1D-myo-inositol + raffinose |
| galactoside 2-alpha-L-fucosyltransferase | GDP-beta-L-fucose + beta-D-galactosyl-(1->3)-N-acetyl-beta-D-glucosaminyl-(1->3)-beta-D-galactosyl-(1->4)-beta-D-glucosyl-(1<—>1)-ceramide |
| glycosaminoglycan galactosyltransferase | UDP-galactose + glycosaminoglycan |
| galactinol-sucrose galactosyltransferase | alpha-D-galactosyl-(1->3)-1D-myo-inositol + sucrose |
| glucosaminylgalactosylglucosylceramide beta-galactosyltransferase | UDP-galactose + N-acetyl-beta-D-glucosaminyl-(1->3)-beta-D-galactosyl-(1->4)-beta-D-glucosyl-(1<—>1)-ceramide |
| N-acetyllactosaminide 3-alpha-galactosyltransferase | UDP-galactose + beta-D-galactosyl-(1->4)-beta-N-acetyl-D-glucosaminyl-R |
| N-acetyllactosamine synthase | UDP-galactose + N-acetyl-D-glucosamine |
| (N-acetylneuraminyl)-galactosylglucosylceramide N-acetylgalactosaminyltransferase | UDP-N-acetyl-D-galactosamine + 1-O-[O-(N-acetyl-alpha-neuraminosyl)-(2->3)-O-beta-D-galactopyranosyl-(1->4)-beta-D-glucopyranosyl]-ceramide |
| sn-glycerol-3-phosphate 1-galactosyltransferase | UDPgalactose + sn-glycerol 3-phosphate |
| glycoprotein-N-acetylgalactosamine 3-beta-galactosyltransferase | UDP-galactose + glycoprotein N-acetyl-D-galactosamine |
| inositol 3-alpha-galactosyltransferase | UDP-D-galactose + myo-inositol |
| xylosylprotein 4-beta-galactosyltransferase | UDP-galactose + O-beta-D-xylosylprotein |
| | UDP-galactose + p-nitrophenyl-beta-D-xyloside |
| | UDP-glucose + 4-methylumbelliferyl-beta-D-xylopyranoside |
| | UDP-xylose + 4-methylumbelliferyl-beta-D-xylopyranoside |
| | UDPgalactose + N-acetyl-beta-D-glucosamine |
| | UDPgalactose + beta-galactosyl-1,4-N-acetyl-beta-D-glucosaminyl-1,6-(N-acetyl-beta-D-glucosaminyl-1,2)-alpha-D-mannosyl-1,6-beta-D-mannosyl-octyl |
| | UDPgalactose + N-acetyl-beta-D-glucosaminyl-1,2-alpha-D-mannosyl-1,6-beta-D-mannosyl-octyl |
| | UDPgalactose + N-acetyl-beta-D-glucosaminyl-1,6-(beta-galactosyl-1,4-N-acetyl-beta-D-glucosaminyl-1,2)-alpha-D-mannosyl-1,6-beta-D-mannosyl-octyl |
| | UDPgalactose + O-beta-D-xylosylprotein |
| | UDPgalactose + p-nitrophenyl N-acetyl-beta-D-glucosaminide |
| | UDPgalactose + xylose |
| galactosylxylosylprotein 3-beta-galactosyltransferase | UDP-galactose + 4-beta-D-galactosyl-O-beta-D-xylosylprotein |
| sn-glycerol-3-phosphate 2-alpha-galactosyltransferase | UDP-galactose + sn-glycerol 3-phosphate |
| indolylacetyl-myo-inositol galactosyltransferase | UDPgalactose + indol-3-ylacetyl-myo-inositol |
| N-acetylneuraminylgalactosylglucosylceramide beta-1,4-N-acetylgalactosaminyltransferase | UDP-N-acetyl-D-galactosamine + N-acetylneuraminyl-(2->3)-alpha-D-galactosyl-(1->4)-beta-D-glucosyl-(1<—>1)-ceramide |
| raffinose-raffinose alpha-galactosyltransferase | raffinose + raffinose |
| sucrose 6F-alpha-galactosyltransferase | UDPgalactose + sucrose |
| lactosylceramide beta-1,3-galactosyltransferase | UDP-galactose + D-galactosyl-(1->4)-beta-D-glucosyl-R |
| galactolipid galactosyltransferase | 2 3-(beta-D-galactosyl)-1,2-diacyl-sn-glycerol |
| galactogen 6beta-galactosyltransferase | UDP-galactose + galactogen |
| 1,3-beta-galactosyl-N-acetylhexosamine phosphorylase | beta-D-galactopyranosyl-(1->3)-N-acetyl-D-glucosamine + phosphate |

TABLE 3-continued

| Enzyme | Substrate |
| --- | --- |
| lactosylceramide 4-alpha-galactosyltransferase | UDP-galactose + beta-D-galactosyl-(1->4)-D-glucosyl-(1<—>1)-ceramide |
| kaempferol 3-O-galactosyltransferase | UDP-galactose + kaempferol = UDP + kaempferol 3-O-beta-D-galactoside |
| digalactosyldiacylglycerol synthase | UDP-galactose + 3-(beta-D-galactosyl)-1,2-diacyl-sn-glycerol = UDP + 3-[alpha-D-galactosyl-(1->6)-beta-D-galactosyl]-1,2-diacyl-sn-glycerol |
| beta-D-galactosyl-(1->4)-L-rhamnose phosphorylase | beta-D-galactosyl-(1->4)-L-rhamnose + phosphate = L-rhamnose + alpha-D-galactose 1-phosphate |
| soyasapogenol B glucuronide galactosyltransferase | UDP-galactose + soyasapogenol B 3-O-beta-D-glucuronide |
| glucosylceramide beta-1,4-galactosyltransferase | UDP-galactose + beta-D-glucosyl-(1<—>1)-ceramide |
| lactotriaosylceramide beta-1,4-galactosyltransferase | UDP-galactose + beta-D-glucosyl-(1<—>1)-ceramide UDP-galactose + N-acetyl-beta-D-galactosaminyl-(1->3)-beta-D-galactosyl-(1->4)-beta-D-glucosyl-(1<—>1)-ceramide |
| cyclin-dependent kinase | ATP + a protein = ADP + a phosphoprotein ATP + ADAQHATPPKKKRKVEDPKDF ATP + amphiphysin I ATP + axonal cytoskeleton protein ATP + axonal cytoskeleton protein ATP + B-cell lymphoma protein 2 |

TABLE 4

| Rule | Specification |
| --- | --- |
| 1 | All candidates have a penta-saccharide code with the sequence Hex-(Hex-Hex-HexNAc-HexNAc. |
| 2 | A DeHex can only be attached to the 1st HexNAc in the core or any HexNAc in the non-reducing end. |
| 3 | Hex and HexNAc can attach up to four antennas. |
| 4 | After the core is complete, HexNAc can attach to any of the three Hex present in the core. |
| 5 | No HexNAc can attach to a HexNAc. |
| 6 | Sialic acid can only be attached to a terminal Hex. However, if all terminal Hex are occupied, it can attach to a HexNAc. |

E. Analyzing Features Across LC-MS/MS Replicate Datasets

Figure 4:
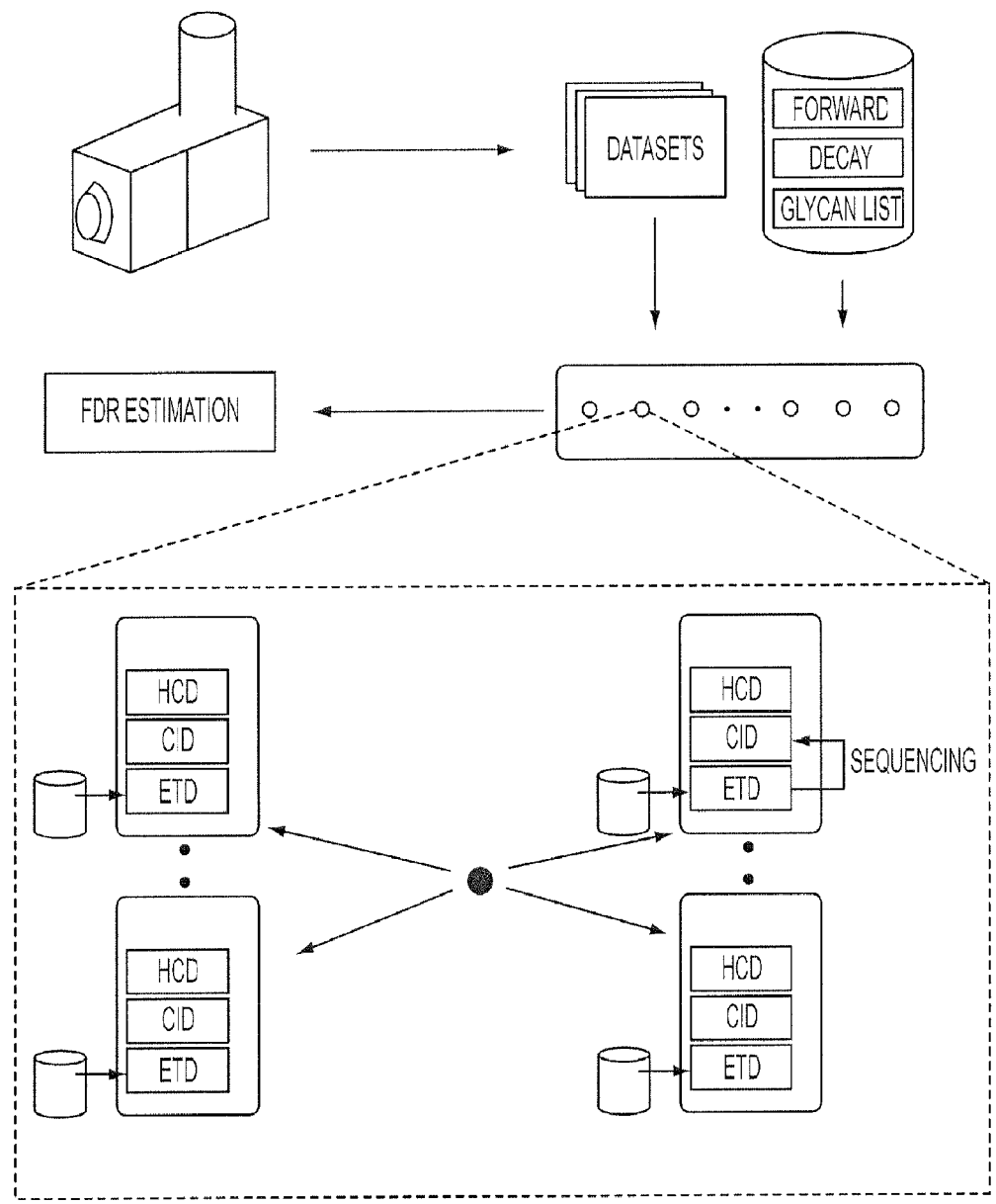
FIG. 4 illustrates one embodiment of a workflow within the presently disclosed framework.

Recently, MS instruments have been developed that are capable of multiple sources of fragmentation in a single run. Previously, runs have typically employed individual or paired (e.g., CID-HCD or CID-ETD) fragmentation. In order to combine fragmentation information for a single glycopeptides, individual datasets must be aligned so that MS/MS information associated with different fragmentation types can be pooled together. The presently disclosed framework implements a functionality to analyze multiple glycoproteomic datasets that were previously aligned, taking an aligned "map" (e.g., from the commercially available MultiAlign software tool), the individual datasets, the target glycoprotein database (as a FASTA file), and a list of glycans as inputs. For instance, the default glycan list described above may be used. Alternatively, a user may define another glycan list. One illustrative embodiment of a workflow within the presently disclosed framework is illustrated in FIG. 4. An aligned map of datasets contains a bunch of LC-MS cluster records, with each one pertaining to a common ion. As a typical map contains thousands of such LC-MC clusters (denoted as circles in FIG. 4), the framework only considers those clusters that are indicative of being a glycopeptide of interest. This determination may be made by matching the mass of each LC-MS cluster record (using a parameterized tolerance of 10 ppm) against a target plus decoy glycopeptide database created from the FASTA file and the glycan list.

Figure 5:
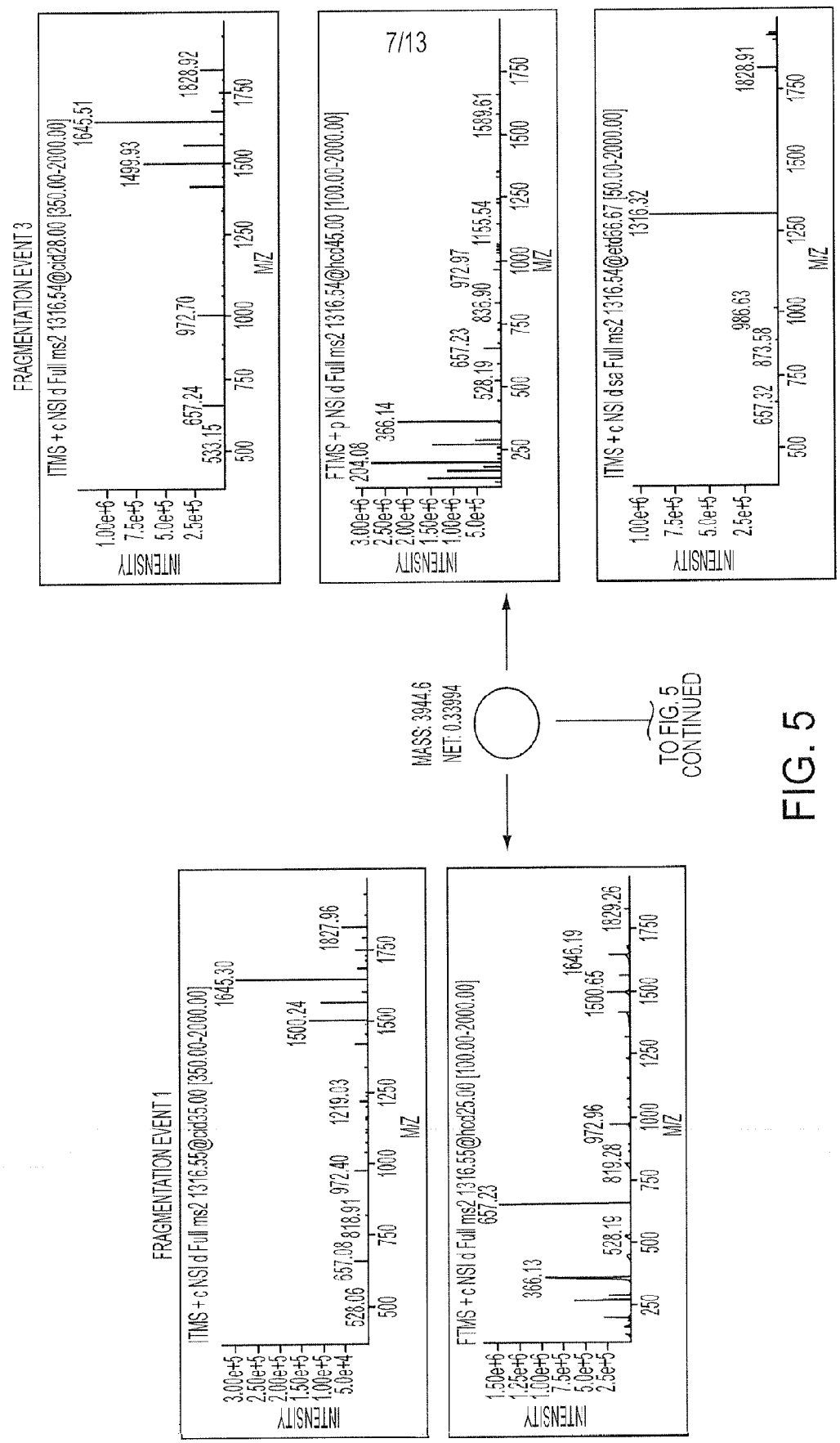
FIG. 5 illustrates one example of fragmentation events for a Fetuin LC-MS cluster.
Figure 5:
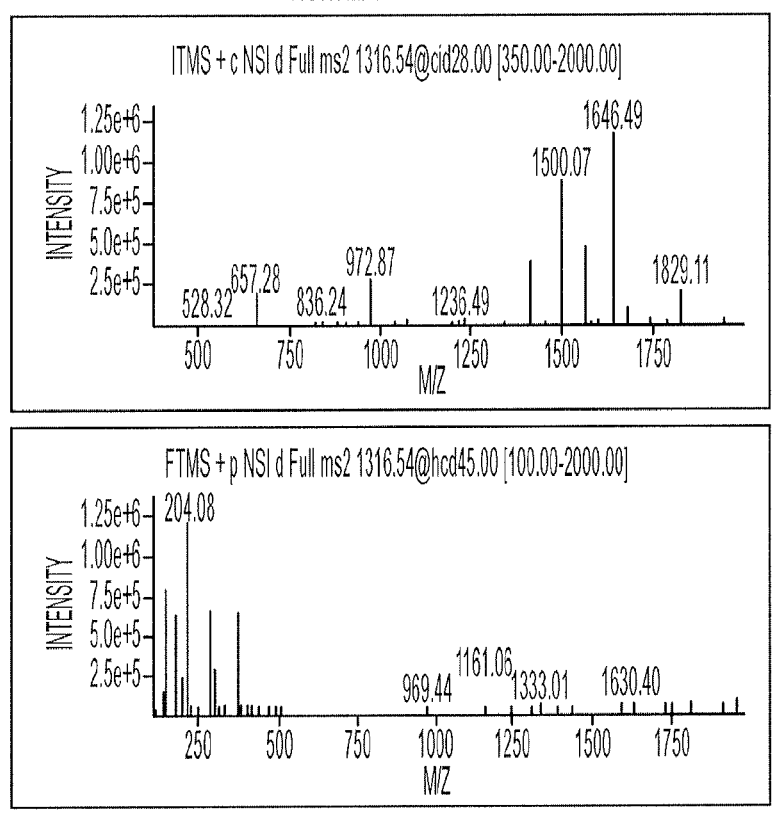

Once a set of candidate glycopeptides is created for a LC-MS record, the presently disclosed framework proceeds to gather fragmentation event information by pooling together MS/MS spectra. Each fragmentation event may comprise a collection of HCD, CID, and ETD MS/MS spectra from a single parent ion within a dataset. FIG. 5 shows one illustrative example for a Fetuin LC-MS cluster with three fragmentation events across three datasets. Two of these fragmentation events have both HCD and CID data, whereas the third has HCD, CID, and ETD data. A typical LC-MS record will have such multiple fragmentation events occurring both within a single dataset (either from different parent ions or the same parent ion but at different elution points within a cluster) and across datasets (as shown in FIG. 5). These events may be scored using a multi-step procedure.

First, all the HCD spectra may be scored one event at a time in order to limit the number of LC-MS records that go into further analysis. As mentioned above, an aligned map may have thousands of LC-MS records, perhaps more in case of complex samples. Filtering using mass to gather only glycopeptides of interest (as discussed above) decreases this number but also results in a large number of false hits. The HCD fragmentation methods appears to be the most sensitive in determining if a particular parent ion was a glycopeptide ion to begin with. Therefore, the presently disclosed framework checks the minimum HCD score across all the fragmentation events; only clusters with a minimum HCD score of less than one (implying one of the seven characteristic peaks have been observed) are considered further. This simple filtering eliminates a large number of false identifications. Second, the framework scores the CID spectra individually for each fragmentation event. Third, the ETD spectrum for each fragmentation event are scored using each candidate glycopeptide and HCD glycan type information (since sialylated vs. non-sialylated compositions can be distinguished based on the HCD spectrum). In the illustrative embodiment, all of the events with their corresponding spectra, the scores, and the identifications are retained within a record for subsequent analysis.

F. Assignment of Glycopeptides in Maps

In traditional proteomics, the concept of peptide spectrum matches (or PSM) is prevalent, where a PSM within a dataset typically contain a one-to-one mapping between peptide and spectrum and receives a single score. The presently disclosed framework instead utilizes a glycopeptide-spectra match (GSM) that contains a one-to-many mapping between a glycopeptide candidate and multiple spectra (e.g., HCD, CID, ETD) and thus receives multiple scores (e.g., HCD score, CID path score, ETD score, CID glycan sequencing score). When both target and decoy glycopeptides are used in the spectrum scoring of a single dataset, a collection of GSMs is obtained, resulting from matching to target glycopeptides (target-GSMs) or from matching to decoy glycopeptides (decoy-GSM). In the illustrative embodiment, each fragmentation event is compiled into a GSM with a corresponding HCD score, a corresponding CID score, the highest ETD scoring glycopeptide, and an associated ETD score. The GSM with the highest ETD score is chosen as the representative (rep-GSM) that either matches a target glycopeptide (target rep-GSM) or a decoy glycopeptide (decoy rep-GSM). Finally, the glycopeptide candidate in each rep-GSM is used with the corresponding CID spectra for glycan sequencing. The sequencing scores may be retained as part of the rep-GSM.

G. Estimating FDR Based on Combined ETD/CID Scoring

Figure 6A:
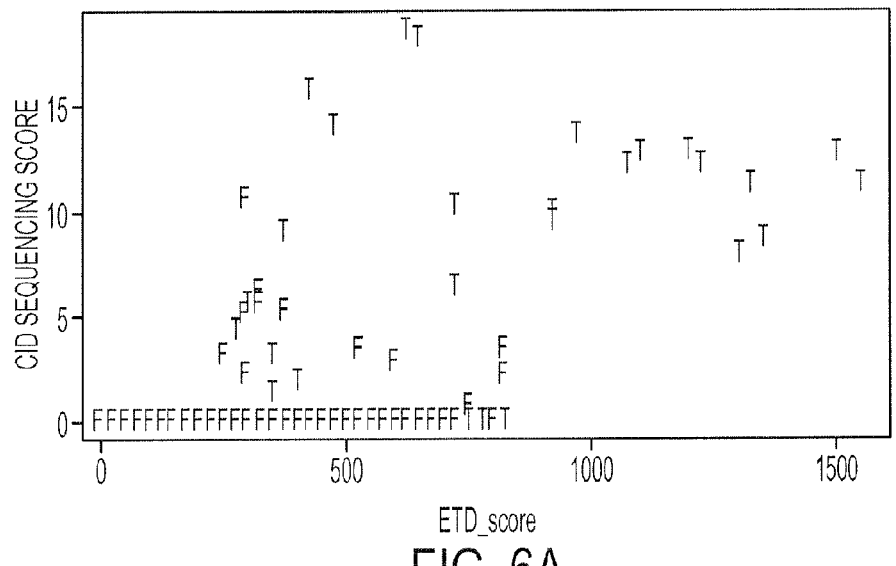
FIG. 6A illustrates one example of a glycomap with both target and decoy representative glycopeptide-spectra matches plotted based on their ETD and CID sequencing scores.

The presently disclosed framework also implements a novel target-decoy search approach for estimating FDR in glycopeptide identification by combining ETD and CID scores of the rep-GSM. FIG. 6A illustrates the principle of this approach on a glycomap created using twelve datasets from the Serum analysis and the SerumMascot dB as the target glycoprotein database. Both target (denoted as 'T') and decoy (denoted as 'F') rep-GSMs are plotted based on their ETD (x-axis) and CID sequencing (y-axis) scores. Most of the target rep-GSMs are located in the top right corner with a high ETD score and a high CID sequencing score, whereas most of the decoy rep-GSMs are located in the bottom left corner of the plot. Such clustering behavior may be exploited by using Linear Discriminant Analysis (LDA). Clustering of target and decoy rep-GSMs was done using the CID sequencing score and the ETD score as the two dimensions. A new score, called an ETD-Sequencing (ES) score, was computed for every rep-GSM using these weights as coefficients. Similar to the ETD FDR approach for a dataset, FDR measures for glycomaps were computed for each rep-GSM (one for each LC-MS record) using the ES score.

Figure 6B:
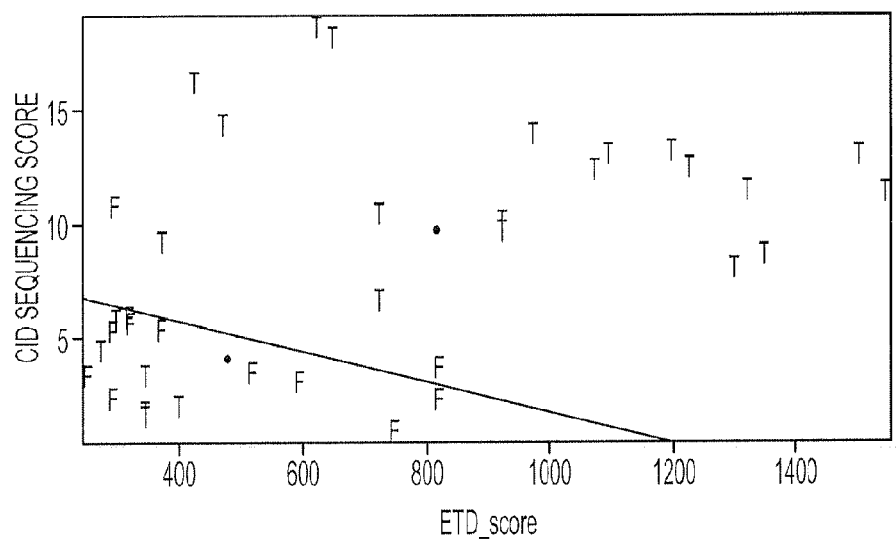
FIG. 6B illustrates a glycomap of non-zero ETD and CID sequencing scores from FIG. 6A with a linear discriminant analysis decision region marked.

FIG. 6B illustrates a 2D-plot for non-zero ETD and CID sequencing scores from FIG. 6A with the LDA decision region marked. The discriminant line created using the projection weights, marked by the decision boundary, was moved across different values of ETD score and CID sequencing score. At each stage, the numbers of False and True hits above the line were noted to get an estimation of FDR. In the illustrative embodiment, the rep-GSMs with FDR less than 0.05 were deemed to be confidently identified (i.e., "Verified") and assigned intact glycopeptides, while the rep-GSMs with FDR equal to or greater than 0.05 were deemed "Tentative." The fragmentation event with the highest ETD score was chosen to be the rep-GSM fragmentation event for both these labels. Those rep-GSMs without any ETD spectra were labeled as "Unverified" and were not involved in FDR estimation. The GSM with the lowest HCD score was chosen as the rep-GSM for these records. Glycopeptide assignments for unverified rep-GSMs were made based on mass and glycan type.

H. Output

The collective information that was obtained for each LC-MS rep-GSM may be printed into an output glycopeptide map, referred to herein as a "glycomap." This glycomap may be illustratively embodied in a comma separated value (CSV) format containing the mass, NET, abundance in datasets, and scores. In other embodiments, the glycomap may be output in an XML format that contains additional information such as dataset specific information and representative spectra in a base 64 format. One example of an XML format glycomap is shown in FIG. 7. The XML format permits additional applications. For example, an experimental CID spectrum of a glycopeptide might be searched against an XML format glycomap to identify glycoforms (i.e., two glycopeptides that contain same peptide but different glycans) within a sample. Additionally, a glycoproteomic dataset run can be simply aligned to the glycomap and glycopeptides identified.

I. Statistical Model for Quantification

In order to estimate glycoprotein differential expression between two sample groups (e.g., cancer and control), an ANOVA-based model was constructed. This model is comprised of terms accounting for glycoproteins, their corresponding peptides (i.e., glycosylation sites), and glycans, along with corresponding interaction terms. Consider a glycomap containing/glycoproteins constructed from a set of N replicate disease and healthy samples. The observed abundance of a particular glycopeptide within glycoprotein i, with a corresponding site j, glycan k, and observed in dataset q is represented as a product term:

$$Y_{i,j(i),k(j(i)),c,q} \sim [P_i, R_{i,c}, F_{j(i)}, G_{k(j(i))}, B_q, E_{i,j(i),k(j(i)),c,q}],$$

where $P_i$ is an abundance of glycoprotein i in a single dataset q, with i=1 ... I, the number of glycoproteins in a sample; $R_{i,c}$ indicates class effect for glycoprotein i indicative of abundance variation across two classes (e.g., cancer and control); $F_{j(i)}$ indicates the site-protein effect indicative of abundance variation of all glycopeptides containing site j in glycoprotein i; $G_{k(j(i))}$ indicates the glycan-site-protein effect indicative of abundance variation of glycopeptide containing glycan k that is attached to glycosylation site j within glycoprotein i; $B_q$ is experiment effect, with q=number of datasets [1 ... N] indicative of total abundance variation on account of experimental conditions; and $E_{i,j(i),k(j(i)),c,q}$ is unmeasured error.

The term j(i) indicates the glycosylation site j in glycoprotein I, and k(j(i)) represents the index of glycans that present at the site j that in-turn is from glycoprotein i thereby indicating nesting. It will be appreciated that "nested" interaction effects are different from "crossed" effects, which consider the effects of all possible glycans with all possible sites within a glycoprotein. The framework is primarily interested in the behavior of particular glycosylated sites with particular glycans between the disease class and the healthy class. In order to build the linear model, the log-2 transformation is done since expression changes are typically multiplicative effects. Thus, the product term above becomes:

$$y_{i,j(i),k(j(i)),c,q} = p_i + r_{i,c} + f_{j(i)} + g_{k(j(i))} + b_1 + e_{i,j(i),k(j(i)),c,q}$$

The model in this equation was solved using an ANOVA-mixed effects model. Each term was considered as a factor and was defined as either fixed or random, as set forth in Table 5 below. The abundance of a glycopeptide can be broken down in contributions from a summation of these factors. Using log likelihood hypothesis testing between a model containing all factors against a null model of only Class and Experiment effect, glycoproteins as well as site-specific glycosylations showing significantly different abundances in disease and control samples can be revealed.

TABLE 5

|  | Description | Type |
|---|---|---|
| Class | Class effect | Fixed |
| protein | Protein effect | Random |
| F | Site: Protein effect | Random |
| G | Glycan: F | Random |
| Experiment | Replicate experiment effect | Random |

III. Experimental Results

Using the illustrative embodiment described above, several glycomaps were built by analyzing datasets from samples of low to high complexity with putative glycoprotein databases as target databases. The summary of all identifications in these glycomaps is given in Table 6 below, which lists the total numbers of glycoproteins, glycosylation sites, and glycopeptides with an estimated FDR less than 0.05. Table 6 also notes the number of glycopeptides for which a complete sequence was derived, and the glycan type distribution for these glycopeptide identifications. Each glycomap analysis is explored individually below. The present disclosure also reports identification numbers for each analysis using a larger size database as a target database. As described further below, the presently disclosed framework gives robust glycopeptide identification even when using a larger target database (containing many more proteins that are not present in the sample), as compared to using an appropriate putative database.

Fetuin_dB database, all five sites corresponding to the two Fetuin proteins along with twenty-two glycopeptides were detected at FDR less than 0.05. However, when the larger Test_dB database (consisting of 71 glycoproteins) was used, only three out these five sites were retained along with eight associated glycopeptides. On the other hand, when the ES scores (each of which integrates an ETD score and an glycan sequencing score) were used, all 5 sites with 10 glycopeptides were identified. This illustrates that even when a larger Test_dB database was used, all five sites corresponding to the Fetuin_A and Fetuin_B proteins were covered, indicating robustness of the framework.

A comparison of ETD scoring and ES_Scoring on the serum map built using the SerumMascot_dB as the target database was also performed. Here, each rep-GSM contains a glycopeptide candidate that has the maximum ETD score. When using only the ETD score, 65 glycopeptides across 33 glycosylation sites from 25 glycoproteins were detected with FDR less than 0.05. The glycopeptide candidate in each rep-GSM was given to the glycan sequencing algorithm, and the corresponding CID sequencing score was recorded. Based on the ETD score and the glycan sequencing score, the ES score was calculated, and corresponding FDR was estimated for each rep-GSM. The number of identifications at less than 0.05 FDR increased significantly (103 glycopeptides across 53 sites in 33 glycoproteins) when using the ES_score, thereby indicating that the combining complementary scoring schemes improved glycopeptide identifications. All analyses discussed below were done using the ES_score model.

TABLE 6

| Glycomap Analysis | No. Protein IDs | No. Sites Detected | No. Glycopeptides | No. Glycopeptides with Glycan Sequences Completely Sequenced | Glycan Class Distribution for Completely Sequenced Glycans | | |
|---|---|---|---|---|---|---|---|
| | | | | | No. Complex | No. High Mannose | No. Hybrid |
| Fetuin (against Fetuin_dB) | 2 | 5 | 22 | 8 | 8 | 0 | 0 |
| 5SG (against 5SG_dB) | 4 | 5 | 11 | 6 | 6 | 0 | 0 |
| Serum (against Serum Mascot_dB) | 33 | 53 | 103 | 94 | 84 | 4 | 6 |

A. Efficacy of ETD Scoring and ES Scoring

In order to test the efficacy of the ETD scoring and the ES_Scoring algorithms described above, the number of identifications (across proteins, glycosylation sites, and glycopeptides) using both scoring schemes on both individual dataset and a map of replicates were compared. A single Fetuin dataset containing HCD, CID and ETD data was analyzed against both the Fetuin_dB and the Test_dB databases (see Table 1 above). The ETD scan corresponding to each GSM for each precursor was matched against candidate target and decoy glycopeptides within 10 ppm of the precursor mass, provided the corresponding HCD score and CID score indicated the presence of a glycopeptide. The highest scoring glycopeptide was recorded as part of the GSM and used in the glycan sequencing algorithm. When only ETD scoring was applied in conjunction with the B. Simple Glycoprotein Study Fetuin glycomaps were built from the Fetuin LC-MS/MS datasets using either Fetuin_dB or Test_dB as a target database. As expected, the number of verified rep-GSMs dropped when using the larger database. Comparing the identifications within these rep-GSMs, however, the most highly scoring proteins were still fetuin in both cases. When Test_dB was used, one glycopeptide of complex N-glycan type is identified in the human Complement 5 protein with high ETD and CID sequencing score, which may correspond to a contaminant glycoprotein in the sample. Nevertheless, 10 out 11 glycopeptides identified from the Test_dB analysis were attributed to fetuin and matched the top 10 out of 22 glycopeptides identified from matching using the Fetuin_dB database. Out of these 22 glycopeptides, eight were completely sequenced and were all sialylated complex structures. All eight completely sequenced glycans matched observed structures in GlycosuiteDB and the CFG database.

C. Mixture Glycoproteins Study

When the standard mixture glycoprotein datasets were analyzed using the 5SG_dB and the Test_dB databases as target databases, the presently disclosed framework identified four out of five glycoproteins in sample with high confidence (FDR<0.05). RNAS1_BOVIN was missed in both cases. Out of a total of eleven glycopeptides, six were completely sequenced and matched with observed structures in external databases, and all eleven glycopeptides were found to be of complex type with sialic-acid terminations. The number of verified rep-GSMs dropped when using the larger database. However, out of eleven glycopeptides identified using the 5SG_dB as the target database, seven were found using the Test_dB without any additional glycopeptides being identified. This again is indicative of the robustness of the ES_Score model.

D. Serum Glycoproteins Study

A serum map was also built using the presently disclosed framework. The default N-glycan list described above was used, but several other glycan lists are available for serum analysis. When the SerumMascot dB was used as a target database, 103 glycopeptides across 53 N-glycosylation sites in 33 glycoproteins were identified at FDR less than 0.05. All but one of the reported glycosylation sites in the glycoproteins identified were confirmed to be annotated by UniprotKB. The glycoprotein HPTR_HUMAN (Haptoglobin-related protein) with a reported glycosylation at site N-126 was not annotated in current UniprotKB. 94 out of 103 glycopeptides were completely sequenced, and a majority (86%) of them were found to be of complex-type. Four high-mannose glycans were identified to be from CO3_HUMAN (Complement C-3) and CO7_HUMAN (Complement C-7) glycoproteins. Out of the six identified glycopeptides with hybrid-type glycans, two were from attachments to N-869 in A2MG_HUMAN (Alpha-2-macroglobulin), two were attached to N-169 in VTNC_HUMAN (Vitronectin), and the remaining two were attached to N-85 in Complement C-3 and at N-271 in A1AT_HUMAN (Alpha-1-Antitrysin). Out of the 84 complex-type glycopeptides, four contained non-sialylated (or a-sialylated) glycans, 26 contained mono-sialylated glycans, 46 contained di-sialylated glycans, and eight contained trisialyated glycans. When the SerumCombined_dB was used as a target database, 34 glycoproteins were found with 50 sites and 89 glycopeptides at FDR less than 0.05. An overlap of 68 glycopeptides was observed between these two analyses. It will be appreciated that, in order to increase coverage, inclusion lists may be built using the tentative and the unverified rep-GSMs. Subsequent rounds of analysis can then be used to delve deeper into the glycoproteome. Irrespective of the complexity of the database and datasets, the scoring schemes (on HCD, CID and ETD spectra) and the overall framework described in the present disclosure are largely robust and ready-to-use.

E. Quantification of Glycoproteins

Figure 8:
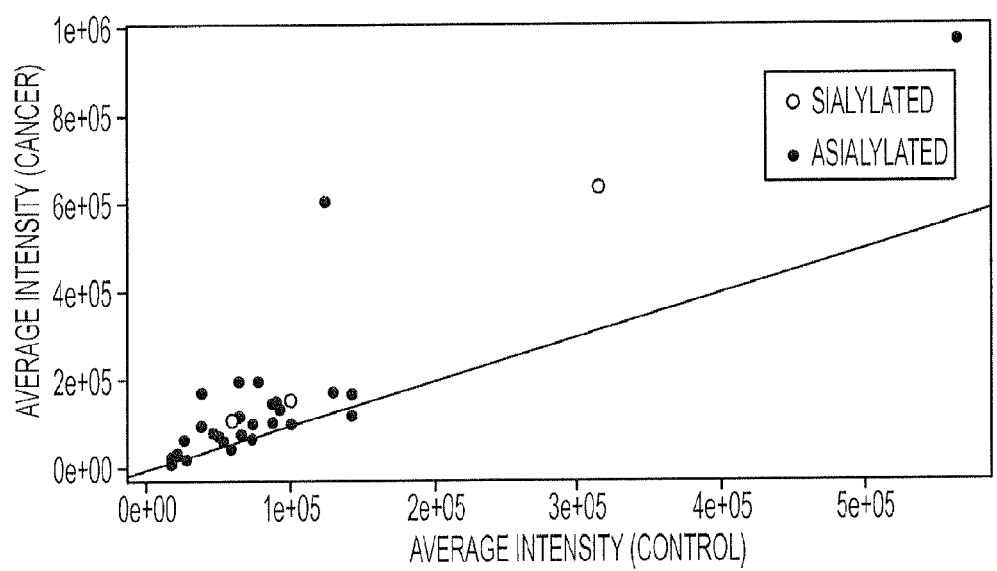
FIG. 8 illustrates one example of a plot of average abundances of glycopeptides between cancer and control samples.

The 103 verified glycopeptides from the serum map built using the SerumMascot_dB database as a target database were analyzed to reveal glycopeptides with significantly different abundances between cancer and control datasets. The datasets containing ETD in both cancer and control groups were ignored since these samples were at a higher concentration. Glycopeptides that were observed in at least three (out of five) replicates in each group were retained. The missing values were imputed using the average of the observed non-zero abundances in the remaining replicates. Additional or different methods of accounting for missing values might be used, in other embodiments. After these filtering and imputation steps, twenty-seven glycopeptides were retained for quantitative analysis. FIG. 8 depicts an illustrative scatter plot of average abundances of glycopeptides between cancer and control groups. The green points are nonsialylated glycopeptides, which on examination were glycopeptides with high-mannose attached glycans from the Complement C-3 glycoprotein (site N-85). All points on the straight line do not show a change in abundance, but the off-line glycopeptides show a differential change between cancer and control. As can be seen, most glycopeptides show an increased abundance in cancer.

In order to detect differential abundances at site-specific levels with a glycoprotein, the twenty-seven glycopeptides were analyzed using the quantification model described herein. The protein, glycosylation site, and glycan effects for each individual glycoprotein were gathered from the glycopeptide assignments made from the serum map. The hypothesis testing for the linear mixed effects model was performed against the null model. The utility of using the mixed effects quantification model is illustrated in FIGS. 9A-D, which each depict glycopeptide abundance profiles between cancer and control for the glycoproteins that were found to be significant (i.e., p-value<0.005). The distribution of glycopeptide abundance across replicates within a group is expressed as a box plot. The box plots for cancer and control replicates are stacked right next to each other. This was done for all glycopeptides identified for a particular glycoprotein, thereby indicating abundance profiles at all sites and glycan levels for a particular glycoprotein within a single plot. The glycan sequences for each glycopeptide were obtained from the sequencing algorithm and then matched to structures pertaining to *homosapiens* that are observed in the CFG database.

Figure 9A:
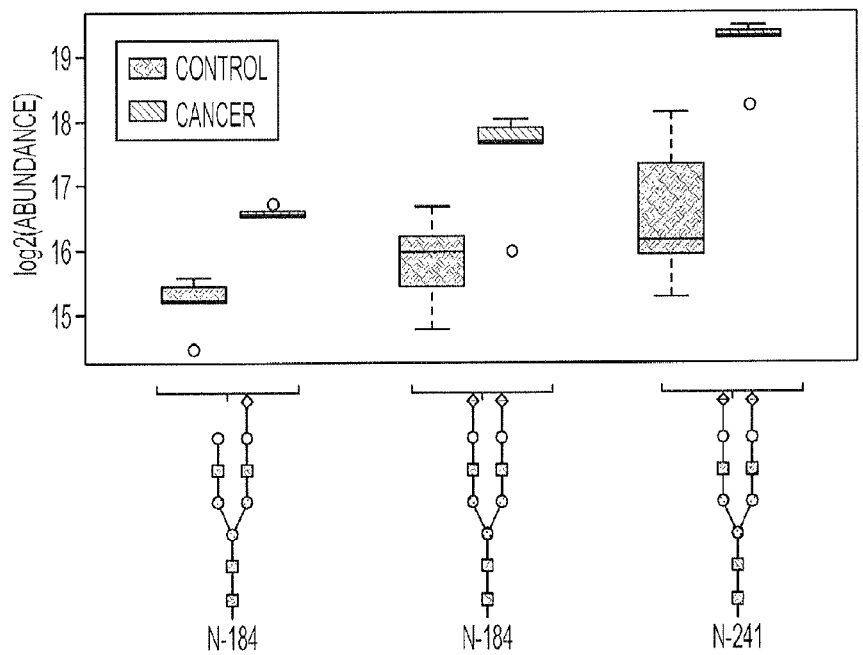
FIGS. 9A-D illustrate glycopeptide abundance profiles between cancer and control samples for various glycoproteins.

In FIG. 9A, abundance profile for glycopeptides from haptoglobin are shown with two glycosylation sites and two sialylated glycans. Although haptoglobin is one of the proteins targeted for depletion by the MARS column, it is not completely depleted on account of secondary interactions with other proteins or homologous proteins. Moreover, if this protein is in higher abundance in one sample then it will not be effectively depleted relative to another sample in which it is less abundant. All haptoglobin glycopeptides were observed to increase in abundance in cancer with the disilylated glycopeptides at site N-184 and N-241 showed a slightly bigger increase than the mono-sialylated one at N-184. Haptoglobin has been previously associated as being increased in inflammatory processes, as well as in ovarian and pancreatic cancer. From the spectral count data collected from a Mascot identification of non-glycosylated peptides, an elevated spectral count was observed for the protein correlating with the increased abundance shown across all quantified glycopeptides.

Figure 9B:
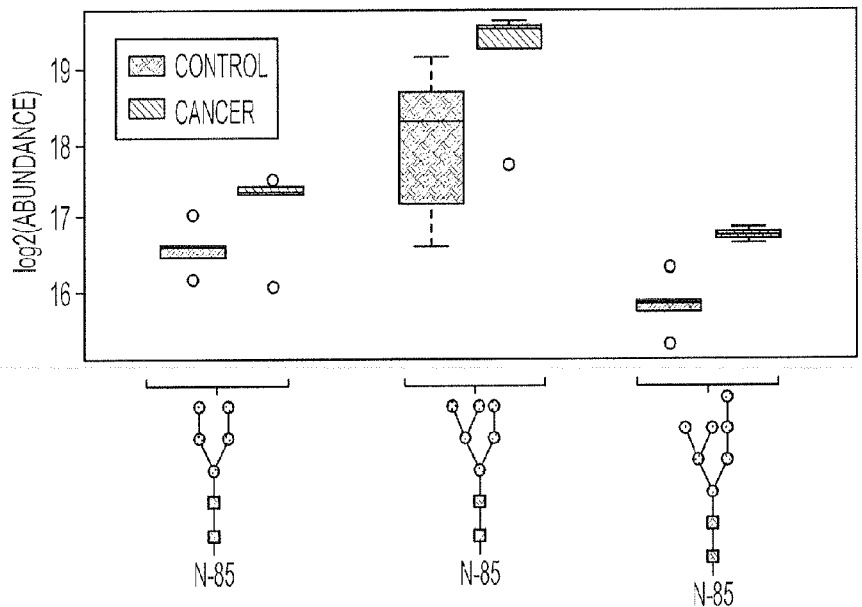

FIG. 9B depicts the same for the glycoprotein CO3_HUMAN (Complement 3 protein) that was found with one glycosylation site (N-85). All sites were attached to glycans of high-mannose type. Again, all glycopeptides showed increased abundance in cancer with a slight variation among them. High-mannose glycans have been associated regularly with elevation in cancer (e.g., breast cancer). Incidentally, the complement C-3 glycoprotein is part of the complement cascade system that has been observed to play a role in cellular proliferation. The increased abundance in esophageal cancer was observed to be consistent at protein level as well from the observations in the spectral count data. Although this protein is of high abundance, the intact glycopeptides are low abundant and show differential glycosylation between cancer and control samples.

Figure 9C:
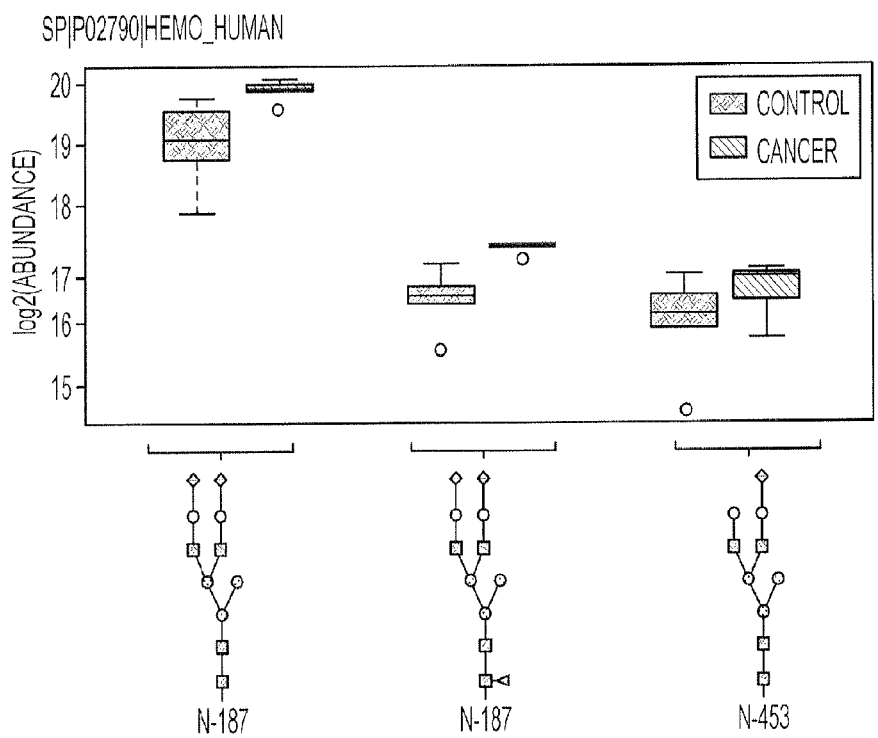

FIG. 9C shows the abundance profile of protein HEMO_HUMAN (Hemopexin), which also indicates overall increase in glycosylation with mono-sialylated structures at site N-453 showing a lesser increase compared to di-sialylated structures at site N-187. The glycoprotein was observed to be abundant as observed from the protein spectral count. Hemopexin is a heme-binding protein whose fucosylated N-linked glycans have been observed to be significantly abundant in hepatocellular carcinoma.

Figure 9D:
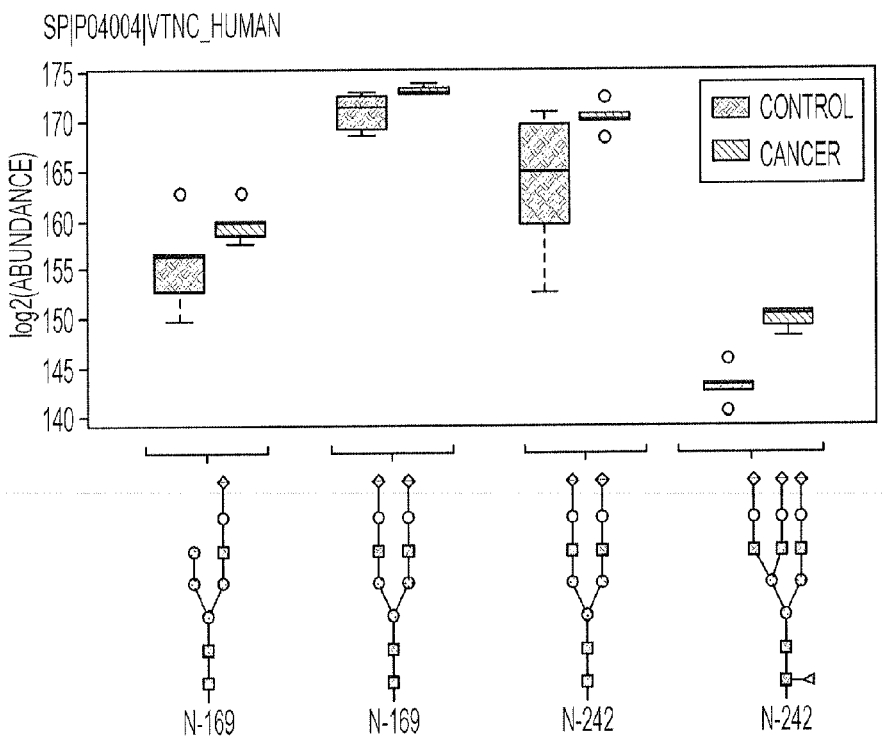

FIG. 9D shows the abundance profile of VTNC_HUMAN (Vitronectin), which shows site-specific differential glycosylation. The increase in the fucosylated tri-sialylated glycopeptide at N-242 between cancer and control appears to be much more than the increase in the disialylated glycopeptide at N-169. A separate study that performed MRM (Multiple Reaction Monitoring) quantitation blood serum glycoproteins enriched by lectin affinity chromatography and hydrazide chemistry also identified hemopexin and vitronectin as highly expressed glycoproteins in cancer with p-value less than 0.05. From the above results, those of skill in the art will appreciate the utility of the presently disclosed framework for selecting biomarker candidates.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure and the appended claims are desired to be protected.

What is claimed is:

1. A method comprising:
   performing electron transfer dissociation (ETD) mass spectrometry on a sample comprising one or more intact glycopeptides by an ETD mass spectrometer to generate ETD mass spectra data representing a plurality of ETD mass spectra;
   constructing, by a computing device, theoretical ETD target mass spectra data representing a plurality of theoretical ETD target mass spectra, wherein each of the plurality of theoretical ETD target mass spectra corresponds to a target glycopeptide of a plurality of target glycopeptides;
   comparing, by the computing device, the ETD mass spectra data with the theoretical ETD target mass spectra data to generate target comparison ETD data indicative of a similarity of each of the plurality of ETD mass spectra to each of the plurality of theoretical ETD target mass spectra associated with a corresponding target glycopeptide of the plurality of target glycopeptides;
   constructing, by the computing device, theoretical ETD decoy mass spectra data representing a plurality of theoretical ETD decoy mass spectra, wherein each of the plurality of theoretical ETD decoy mass spectra corresponds to a decoy glycopeptide of a plurality of decoy glycopeptides;
   comparing, by the computing device, the ETD mass spectra data with the theoretical ETD decoy mass spectra data to generate decoy comparison ETD data indicative of a similarity of each of the plurality of ETD mass spectra to each of the plurality of theoretical ETD decoy mass spectra associated with a corresponding decoy glycopeptide of the plurality of decoy glycopeptides; and
   estimating, by the computing device, a false discovery rate (FDR) based at least in part on the target comparison ETD data and the decoy comparison ETD data, wherein the FDR comprises a ratio of a number of data points of the decoy comparison ETD data that exceed a threshold to a total number of data points of the decoy comparison ETD data and of the target comparison ETD data that exceed the threshold.

2. The method of claim 1, wherein each of the one or more intact glycopeptides comprises one or more glycans attached to a peptide.

3. The method of claim 1, wherein the one or more intact glycopeptides comprise an N-linked glycopeptide.

4. The method of claim 1, wherein the one or more intact glycopeptides comprise an O-linked glycopeptide.

5. The method of claim 1, wherein the sample is a complex sample comprising a plurality of intact glycopeptides.

6. The method of claim 1, further comprising:
   performing collision-induced dissociation (CID) mass spectrometry on the sample to generate CID data representing a plurality of CID mass spectra obtained after CID fragmentation; and
   performing high-energy C-trap dissociation (HCD) mass spectrometry on the sample to generate HCD data representing a plurality of HCD mass spectra obtained after HCD fragmentation.

7. The method of claim 6, further comprising:
   determining, by the computing device and based on the HCD data, a distribution of a plurality of characteristic ions in the plurality of HCD mass spectra; and
   determining, by the computing device and based on the distribution, whether one or more of the plurality of characteristic ions is a glycopeptide ion.

8. The method of claim 1, further comprising quantifying an abundance of one or more intact glycopeptides of the sample.

9. The method of claim 8, wherein quantifying the abundance of one or more intact glycopeptides comprises determining a spectral count of the one or more intact glycopeptides of the sample.

10. The method of claim 8, wherein the abundance of one or more intact glycopeptides in the sample is increased in a sample associated with cancer as compared to a control sample.

11. One or more computer-readable media comprising a plurality of instructions that, in response to being executed by one or more processors, result in the one or more processors:
    receiving, from an ETD mass spectrometer, ETD mass spectra data representing a plurality of ETD mass spectra obtained from ETD mass spectrometry of a sample comprising one or more intact glycopeptides by the ETD mass spectrometer;
    constructing theoretical ETD target mass spectra data representing a plurality of theoretical ETD target mass spectra, wherein each of the plurality of theoretical ETD target mass spectra corresponds to a target glycopeptide of a plurality of target glycopeptides;
    comparing the ETD mass spectra data with the theoretical ETD target mass spectra data to generate target comparison ETD data indicative of a similarity of each of the plurality of ETD mass spectra to each of the plurality of theoretical ETD target mass spectra associated with a corresponding target glycopeptide of the plurality of target glycopeptides;

constructing theoretical ETD decoy mass spectra data representing a plurality of ETD decoy mass spectra representing a plurality of theoretical ETD decoy mass spectra, wherein each of the plurality of theoretical ETD decoy mass spectra corresponds to a decoy glycopeptide of a plurality of decoy glycopeptides;

comparing the ETD mass spectra data with the theoretical ETD decoy mass spectra data to generate decoy comparison ETD data indicative of a similarity of each of the plurality of ETD mass spectra to each of the plurality of theoretical ETD decoy mass spectra associated with a corresponding decoy glycopeptide of the plurality of decoy glycopeptides; and estimating a false discovery rate (FDR) based at least in part on the target comparison ETD data and the decoy comparison ETD data, wherein the FDR comprises a ratio of a number of data points of the decoy comparison ETD data that exceed a threshold to a total number of data points of the decoy comparison ETD data and of the target comparison ETD data that exceed the threshold.

12. The one or more computer-readable media of claim 11, wherein the plurality of instructions, in response to being executed by the one or more processors, further result in at least one of the one or more processors controlling operation of the ETD mass spectrometer to generate the ETD mass spectra data.

13. The one or more computer-readable media of claim 11, wherein each of the one or more intact glycopeptides comprises one or more glycans attached to a peptide.

14. The one or more computer-readable media of claim 11, wherein the one or more intact glycopeptides comprise an N-linked glycopeptide.

15. The one or more computer-readable media of claim 11, wherein the one or more intact glycopeptides comprise an O-linked glycopeptide.

16. The one or more computer-readable media of claim 11, wherein the sample is a complex sample comprising a plurality of intact glycopeptides.

17. The one or more computer-readable media of claim 11, wherein the plurality of instructions, in response to being executed by the one or more processors, further result in the one or more processors:

performing collision-induced dissociation (CID) mass spectrometry on the sample to generate CID data representing a plurality of CID mass spectra obtained after CID fragmentation; and performing high-energy C-trap dissociation (HCD) mass spectrometry on the sample to generate HCD data representing a plurality of HCD mass spectra obtained after HCD fragmentation.

18. The one or more computer-readable media of claim 17, wherein the plurality of instructions, in response to being executed by the one or more processors, further result in the one or more processors:

determining, by the computing device and based on the HCD data, a distribution of a plurality of characteristic ions in the plurality of HCD mass spectra; and determining, by the computing device and based on the distribution, whether one or more of the plurality of characteristic ions is a glycopeptide ion.

19. The one or more computer-readable media of claim 11, wherein the plurality of instructions, in response to being executed by the one or more processors, further result in the one or more processors quantifying an abundance of one or more intact glycopeptides of the sample.

20. The one or more computer-readable media of claim 19, wherein quantifying the abundance of one or more intact glycopeptides comprises determining a spectral count of the one or more intact glycopeptides of the sample.

21. The one or more computer-readable media of claim 19, wherein the abundance of one or more intact glycopeptides in the sample is increased in a sample associated with cancer as compared to a control sample.

* * * * *